US011795276B2

(12) United States Patent
Iwasaki

(10) Patent No.: US 11,795,276 B2
(45) Date of Patent: Oct. 24, 2023

(54) COMPOSITE PARTICLES, COMPOSITE PARTICLES FOR FORMING LIQUID-ENCAPSULATING PARTICLES, LIQUID-ENCAPSULATING PARTICLES, METHOD FOR PRODUCING LIQUID-ENCAPSULATING PARTICLES, BIOCATALYST-CONTAINING MATERIAL, BIOCATALYST-CONTAINING MATERIAL PRODUCING APPARATUS, AND BIOCATALYST-CONTAINING MATERIAL PRODUCING METHOD

(71) Applicant: RICOH COMPANY, LTD., Tokyo (JP)

(72) Inventor: Koji Iwasaki, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 595 days.

(21) Appl. No.: 16/943,570

(22) Filed: Jul. 30, 2020

(65) Prior Publication Data

US 2021/0032414 A1 Feb. 4, 2021

(30) Foreign Application Priority Data

Jul. 31, 2019 (JP) ................................ 2019-141316
Jul. 31, 2019 (JP) ................................ 2019-141318
(Continued)

(51) Int. Cl.
*C08J 3/12* (2006.01)
*C08K 3/36* (2006.01)
(Continued)

(52) U.S. Cl.
CPC ............... *C08J 3/128* (2013.01); *C08J 3/126* (2013.01); *C08K 3/22* (2013.01); *C08K 3/36* (2013.01);
(Continued)

(58) Field of Classification Search
CPC ................................ B82Y 30/00; C08J 3/128
See application file for complete search history.

(56) References Cited

U.S. PATENT DOCUMENTS

2016/0068671 A1 3/2016 Yamabe et al.
2016/0223928 A1 8/2016 Miyao et al.
(Continued)

FOREIGN PATENT DOCUMENTS

JP 2005-202133 A 7/2005
JP 2014-214286 A 11/2014
(Continued)

OTHER PUBLICATIONS

European Communication pursuant to Article 94(3) EPC dated Dec. 5, 2022, in European Application No. 20188462.4., 10 pages.
(Continued)

*Primary Examiner* — Alexandre F Ferre
(74) *Attorney, Agent, or Firm* — Grüneberg and Myers PLLC

(57) ABSTRACT

Provided are composite particles including hydrophobic solid particle A and hydrophobic solid particle B over surface of hydrophobic solid particle A, wherein contact angle CAa of hydrophobic solid particle A with water is 110 degrees≤CAa≤180 degrees, contact angle CAb of hydrophobic solid particle B with water is 110 degrees≤CAb≤180 degrees, ratio (d50a/d50b) of number average particle diameter d50a of hydrophobic solid particle A to number average particle diameter d50b of hydrophobic solid particle B is 10≤(d50a/d50b)≤100, and coating ratio CR of composite particles expressed by Formula 1 is 50%≤CR≤500%,
(Continued)

Formula 1

Coating ratio $CR$ (%) =

$$\frac{\pi(d50b/2)^2}{4\pi(d50a/2+d50b/2)^2}\times\frac{\{X_b(g)/Y_b(g/\mu m^3)/Z_b(\mu m^3)\}}{\{X_a(g)/Y_a(g/\mu m^3)/Z_a(\mu m^3)\}}\times 100$$

where in Formula 1, Xa, Ya, and Za represent mass (g), density (g/cubic micrometer), and volume (cubic micrometer) of hydrophobic solid particle A, and Xb, Yb, and Zb represent mass (g), density (g/cubic micrometer), and volume (cubic micrometer) of hydrophobic solid particle B.

18 Claims, 6 Drawing Sheets

(30) Foreign Application Priority Data

Jul. 28, 2020 (JP) ................................ 2020-126993
Jul. 28, 2020 (JP) ................................ 2020-127046

(51) Int. Cl.
*C12N 1/00* (2006.01)
*C12N 1/16* (2006.01)
*C08K 3/22* (2006.01)
*C08K 5/06* (2006.01)

(52) U.S. Cl.
CPC ................ *C08K 5/06* (2013.01); *C12N 1/005* (2013.01); *C12N 1/16* (2013.01); *C08J 2327/18* (2013.01); *C08K 2003/2237* (2013.01); *C08K 2201/003* (2013.01); *C08K 2201/013* (2013.01)

(56) References Cited

U.S. PATENT DOCUMENTS

| | | | |
|---|---|---|---|
| 2017/0051188 | A1 | 2/2017 | Fujii et al. |
| 2018/0201713 | A1 | 7/2018 | Iwasaki |
| 2018/0273658 | A1 | 9/2018 | Iwasaki |
| 2018/0275433 | A1 | 9/2018 | Iwasaki |

FOREIGN PATENT DOCUMENTS

| | | | |
|---|---|---|---|
| WO | WO 86/02093 | A1 | 4/1986 |
| WO | WO2015/129903 | A1 | 9/2015 |

OTHER PUBLICATIONS

Lefebvre G. et al., "Dry coating of talc particles with fumed silica: Influence of the silica concentration on the wettability and dispersibility of the composite particles", Powder Technology, vol. 208, No. 2, 2008, pp. 372-377.

Chinese Office Action dated Jun. 30, 2021 in Chinese Application No. 2020107558048, with English translation, 13 pages.

Nathan Pike et al. "How aphids lose their marbles", Proc. R. Soc. Lond. B (2002) 269, 1211-1215.

Keiji Igarashi et al. "A New Water-in-Powder Technology: A Novel Structure for Creating Unique Cosmetic Products", J. Soc. Cosmet. Chem. Jpn. Report 42 (4) 313-318 (2008) (with English Abstract).

Junfei Tian et al. "Respirable liquid marble for the cultivation of microorganisms", Colloids and Surfaces B: Biointerfaces 106 (2013) 187-190.

Extended European Search Report dated Dec. 14, 2020 in European Patent Application No. 20188462.4, citing documents AA, AO-AQ, and AX therein, 12 pages.

Jui Hun Chen, et al., "Synthesis ZnO/polystyrene composites particles by Pickering emulsion polymerization," European Polymer Journal, vol. 44, 2008, pp. 3271-3279.

COMPOSITE PARTICLES, COMPOSITE PARTICLES FOR FORMING LIQUID-ENCAPSULATING PARTICLES, LIQUID-ENCAPSULATING PARTICLES, METHOD FOR PRODUCING LIQUID-ENCAPSULATING PARTICLES, BIOCATALYST-CONTAINING MATERIAL, BIOCATALYST-CONTAINING MATERIAL PRODUCING APPARATUS, AND BIOCATALYST-CONTAINING MATERIAL PRODUCING METHOD

CROSS-REFERENCE TO RELATED APPLICATIONS

The present application claims priority under 35 U.S.C. § 119 to Japanese Patent Application No. 2019-141316 filed Jul. 31, 2019, Japanese Patent Application No. 2019-141318 filed Jul. 31, 2019, Japanese Patent Application No. 2020-126993 filed Jul. 28, 2020, and Japanese Patent Application No. 2020-127046 filed Jul. 28, 2020. The contents of which are incorporated herein by reference in their entirety.

BACKGROUND OF THE INVENTION

Field of the Invention

The present disclosure relates to composite particles, composite particles for forming liquid-encapsulating particles, liquid-encapsulating particles, a method for producing liquid-encapsulating particles, a biocatalyst-containing material, a biocatalyst-containing material producing apparatus, and a biocatalyst-containing material producing method.

Description of the Related Art

With pressure or temperature changes, industrially applicable materials become able to be handled stably in any of a gas phase, a liquid phase, and a solid phase. However, in terms of handleability of materials during, for example, transportation, gases need to be taken care of so as not to leak, and cannot be handled efficiently because gases have low densities. Liquids need to be taken care of so as not to leak, and cannot be handled efficiently because liquids may contaminate the transportation paths. Therefore, solids are preferable in terms of handleability of materials.

Hence, in order to handle materials in the form of solids, known existing techniques solidify gases and liquids by cooling, or adsorb gases and liquids to porous materials. However, these techniques need cooling energy, and the industrially applicable scopes are limited.

In recent years, as techniques for handling materials without phase changes, liquid marbles produced by, for example, aphids have been paid attention. Aphids are known to remove droplets of honeydew secreted from inside the bodies to outside the nests by coating the surfaces of the droplets with hydrophobic particles, and handle liquids like solids (for example, see Proc. R. Soc. Lond. B (2002) 269, 1211-1215). As a technique for forming liquid marbles by mimicking and industrially applying the said liquid marbles, a reported technique coats the surfaces of liquid droplets, which are formed of a lotion component, with particles having a specific wettability (a contact angle with water) to form liquid-encapsulating particles (for example, see J. Soc. Cosmet. Chem. Jpn. Report 42 (4) 313-318 (2008)). A proposed particle-shaped adhesive is formed of a liquid droplet-shaped adhesive component, of which surface is coated with hydrophobic particles (for example, see International Publication No. WO 2015/129903).

SUMMARY OF THE INVENTION

According to an aspect of the present disclosure, composite particles include a hydrophobic solid particle A and a hydrophobic solid particle B over the surface of the hydrophobic solid particle A. The contact angle CAa of the hydrophobic solid particle A with water is 110 degrees or greater but 180 degrees or less. The contact angle CAb of the hydrophobic solid particle B with water is 110 degrees or greater but 180 degrees or less. The ratio (d50a/d50b) of the number average particle diameter d50a of the hydrophobic solid particle A to the number average particle diameter d50b of the hydrophobic solid particle B is 10 or greater but 100 or less. The coating ratio CR of the composite particles expressed by Formula 1 below is 50% or higher but 500% or lower.

Formula 1

$$\text{Coating ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

DESCRIPTION OF THE EMBODIMENTS (Composite Particles)

Figure 1A:
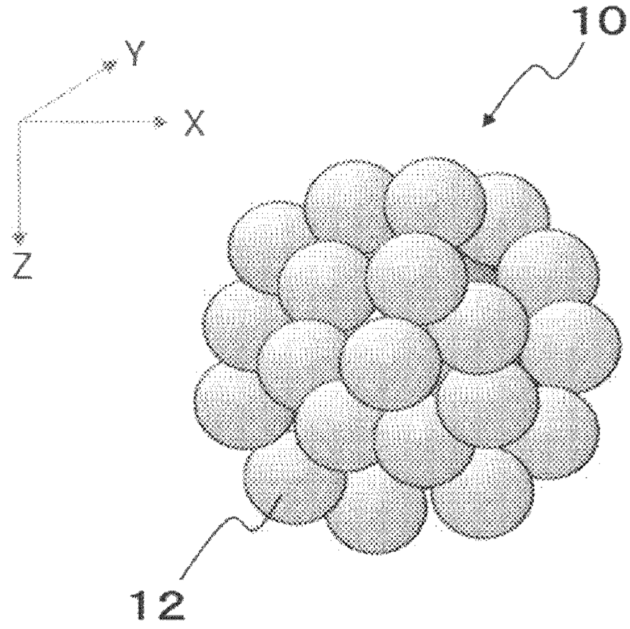
FIG. 1A is an exemplary view illustrating an example of composite particles of the present disclosure.

Composite particles of the present disclosure include a hydrophobic solid particle A and a hydrophobic solid particle B.

Composite particles of the present disclosure include the hydrophobic solid particle A and the hydrophobic solid particle B over the surface of the hydrophobic solid particle A. The hydrophobic solid particle A has a contact angle CAa of 110 degrees or greater but 180 degrees or less with water. The hydrophobic solid particle B has a contact angle CAb of 110 degrees or greater but 180 degrees or less with water. The ratio (d50a/d50b) of the number average particle diameter d50a of the hydrophobic solid particle A to the number average particle diameter d50b of the hydrophobic solid particle B is 10 or greater but 100 or less. The coating ratio CR of the composite particles expressed by Formula 1 below is 50% or higher but 500% or lower. The composite particles further include other components as needed.

Formula 1

$$\text{Coating ratio } CR\ (\%) = \frac{\pi(d50b/2)^2}{4\pi(d50a/2 + d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

Existing techniques for producing particles of lotions have succeeded in designing the particles for being applied on skin in an adequate amount and rubbed against skin for the lotion component to be released outside the particles, but as a trade-off to this convenience, have a problem that the particles can easily collapse in response to external forces (for example, impacts during transportation).

Existing techniques for coating adhesive compositions with particles can provide durability against impacts during transportation, but has a problem that the techniques cannot be applied to a wide variety of liquids because the durability is mainly attributable to the high viscosity unique to liquid components.

Hence, the present inventor has studied particles that suppress coalescing of liquid droplets of various kinds of liquids and have an excellent durability against external forces, and have obtained the following findings.

The present inventor has found that liquid droplet-encapsulating particles (may be referred to as liquid marbles or liquid-encapsulating particles) produced only with particles having a large particle diameter have a small contact area between the particles coating the liquid droplets and the liquid droplets, to have the liquid droplets exposed at some positions, leading to a very poor strength against external forces and difficulty with improving durability.

The present inventor has also found that liquid-encapsulating particles produced only with particles having a small particle diameter have a better durability against external forces, but are easily deformable, leading to a problem that the liquid-encapsulating particles may coalesce with each other due to a capillary phenomenon.

Hence, the present inventor has found that use of two kinds of hydrophobic solid particles having a specific property and having different particle diameters (hydrophobic solid particles A having a greater particle diameter and hydrophobic solid particles B having a smaller particle diameter) makes it possible to suppress coalescing of liquid-encapsulating particles.

The present inventor has also found that composite particles in which the hydrophobic solid particles B are distributed over the surface of the hydrophobic solid particles A can suppress coalescing of liquid-encapsulating particles, can coat the surfaces of liquid droplets of various kinds of liquids, and can form liquid-encapsulating particles having an excellent durability.

The present disclosure has an object to provide composite particles that can suppress coalescing of liquid droplets of various kinds of liquids and can form liquid-encapsulating particles having an excellent durability against external forces.

The present disclosure can provide composite particles that can suppress coalescing of liquid droplets of various kinds of liquids and can form liquid-encapsulating particles having an excellent durability against external forces.

—Hydrophobic Solid Particle a and Hydrophobic Solid Particle B—

The hydrophobic solid particle B is present over the surface of the hydrophobic solid particle A and coats the surface of the hydrophobic solid particle A. The hydrophobic solid particle B coating the surface of the hydrophobic solid particle A means that the hydrophobic solid particle B coats the surface of the hydrophobic solid particle A enough to enable the effect of the present disclosure to be achieved, and that the hydrophobic solid particle B coats the surface of the hydrophobic solid particle A in a manner to satisfy a coating ratio CR described below.

In the present disclosure, "the surface of the hydrophobic solid particle A" means the exposed surface of the hydrophobic solid particle A.

The hydrophobic solid particle A has a contact angle CAa of 110 degrees or greater but 180 degrees or less with water. The hydrophobic solid particle B has a contact angle CAb of 110 degrees or greater but 180 degrees or less with water.

When the contact angles CAa and CAb with water are 110 degrees or greater but 180 degrees or less, coalescing of liquid-encapsulating particles can be suppressed.

In the present disclosure, "hydrophobicity" means a contact angle CAa and a contact angle CAb of 90 degrees or greater but 180 degrees or less with water when measured by a method for measuring the contact angles described below.

With respect to a solution containing water in an amount of 15% by mass or greater, the hydrophobic solid particle A has a contact angle CALa of 100 degrees or greater but 180 degrees or less with the solution, and the hydrophobic solid particle B has a contact angle CALb of 100 degrees or greater but 180 degrees or less with the solution. It is preferable that the hydrophobic solid particle A have a contact angle CALa of 100 degrees or greater but 160 degrees or less with the solution containing water in an amount of 15% by mass or greater, and that the hydrophobic solid particle B have a contact angle CALb of 100 degrees or greater but 160 degrees or less with the solution containing water in an amount of 15% by mass or greater.

When the contact angles CALa and CALb of the hydrophobic solid particle A and the hydrophobic solid particle B with the solution are 100 degrees or greater but 180 degrees or less, coalescing of liquid-encapsulating particles can be suppressed.

The solution is not particularly limited and may be appropriately selected depending on the intended purpose so long as the solution contains water in an amount of 15% by mass or greater. Examples of the solution include saline, a cell culture medium, and a glucose solution. Other substances that may be contained are not particularly limited and may be appropriately selected depending on the intended purpose. Examples of the substances include a water-soluble compound, a water-insoluble compound, a food additive, and a physiologically active substance.

Examples of the water-soluble compound include glucose, ascorbic acid, Japanese Pharmacopoeia honey, 1-ethyl-3-methyl imidazolium trifluoromethane sulfonate ([EMIM][CF3SO3]), 1-butyl-3-methyl imidazolium trifluoromethane sulfonate ([BMIM][CF3SO3]), (1-butyl-3-methyl imidazolium=chloride ([BMIM][Cl]), glycerin, polyglycerin, and lactose.

Examples of the water-insoluble compound include inorganic fillers such as titanium oxide, activated carbon, zeolite, and silica.

Examples of the food additive include antioxidants such as L-sodium ascorbate, and a fungicide.

Examples of the physiologically active substance include: vitamins such as vitamin B1 and folic acid, and amino acids such as arginine and alanine.

As the method for measuring the contact angles CAa and CAb with water, a plate-shaped body obtained by hot-pressing the material constituting the hydrophobic solid particle A or B or a plate-shaped body obtained by casting a dispersion liquid of the material constituting the hydrophobic solid particle A or B over a substrate by a casting method is used as the sample to be measured, and the angle formed between the liquid surface of water and the surface of the plate-shaped body when the water is located in an amount of 10 microliters over the sample with a microsyringe is measured as the contact angle CAa or CAb with the water (according to a known contact angle measuring method (θ/2 method)). With the water changed to the solution, the measuring method described above can be used as the method for measuring the contact angles CALa and CALb with the solution.

The conditions of the hot-pressing when producing the plate-shaped body by hot-pressing the material constituting the hydrophobic solid particle A or B are as follows.

[Hot-Pressing Conditions]

Temperature: 200 degrees C.

Total pressure applied: 30 kN

Time: for 5 minutes from when the pressure reaches 30 kN

Operation: A powder of the sample (the material constituting the hydrophobic solid particle) is filled in a powder compacting die having an internal diameter of 10 mm and a depth of 20 mm until the height of the powder from the bottom reaches 10 mm, and set in a press machine (machine name: SA302 DESK-TOP TEST PRESS, available from Tester Sangyo Co., Ltd.). After it is confirmed that the die has reached a predetermined temperature (200 degrees C.), pressing is started up to a predetermined pressure (30 kN). The material is pressed for 5 minutes from when the pressure reaches the predetermined pressure. In this way, the sample is produced.

The plate-shaped body obtained by casting a dispersion liquid of the material constituting the hydrophobic solid particle A or B over a substrate by a casting method is obtained by the hot-pressing described above on a powder of the sample (the material constituting the hydrophobic solid particle) approximately uniformly sprinkled over PTFE (polytetrafluoroethylene, with an average thickness of 200 micrometers) that is punched to have a diameter of 10 mm and set on the powder compacting die in the production of the plate-shaped body by the hot-pressing of the material constituting the hydrophobic solid particle A or B.

The method for approximately uniformly sprinkling the powder of the sample (the material constituting the hydrophobic solid particle) is not particularly limited and may be approximately selected depending on the intended purpose. Examples of the method include a method of sprinkling a dry sample powder, and a method of sprinkling a sample dispersion liquid. A solvent used in the sample dispersion liquid is not particularly limited and may be appropriately selected depending on the intended purpose. Examples of the solvent include ethanol. When the sample dispersion liquid is used, it is easy to handle a sample having a low bulk density.

When using the materials constituting the hydrophobic solid particle A and the hydrophobic solid particle B of the composite particles as the samples to be measured, the materials of the hydrophobic solid particle A and the hydrophobic solid particle B may be identified by, for example, gas chromatography (GC-MS), nuclear magnetic resonance (NMR), and infrared spectroscopy (IR) to procure the materials and measure the contact angles CAa and CAb with the water using the procured materials, or the hydrophobic solid particle A and the hydrophobic solid particle B may be isolated from the composite particles to produce the plate-shaped body using the hydrophobic solid particle A or hydrophobic solid particle B isolated and measure the contact angles CAa and CAb with the water. With the water changed to the solution, the measuring method described above can be used as the method for measuring the contact angles CALa and CALb with the solution.

Examples of the method for isolating the hydrophobic solid particle A and the hydrophobic solid particle B from the composite particles include a method of filtrating a dispersion liquid of the composite particles obtained by adding an alcohol (for example, ethanol and isopropanol) to the composite particles. Of these alcohols, ethanol is preferable. Ethanol is preferable because of a high volatility that facilitates drying after filtration.

The ratio (d50a/d50b) of the number average particle diameter d50a of the hydrophobic solid particles A to the number average particle diameter d50b of the hydrophobic solid particles B is 10 or greater but 100 or less.

The number average particle diameter d50a of the hydrophobic solid particles A and the number average particle diameter d50b of the hydrophobic solid particles B are each the average of longest diameters of ten particles arbitrarily selected from a scanning electron microscopic image of the hydrophobic solid particles A or the hydrophobic solid particles B isolated by the method described above and observed by bulk.

The ratio (d50a/d50b) of the number average particle diameter d50a of the hydrophobic solid particles A to the number average particle diameter d50b of the hydrophobic solid particles B is 10 or greater but 100 or less, and preferably 30 or greater but 50 or less. When the ratio (d50a/d50b) of the number average particle diameter d50a of the hydrophobic solid particles A to the number average particle diameter d50b of the hydrophobic solid particles B is 10 or greater but 100 or less, liquid-encapsulating particles excellent in coalescing suppressibility and durability against external forces can be formed. When the ratio (d50a/d50b) of the number average particle diameter d50a of the hydrophobic solid particles A to the number average particle diameter d50b of the hydrophobic solid particles B is less than 10, it is difficult to form composite particles. When the ratio (d50a/d50b) of the number average particle diameter d50a of the hydrophobic solid particles A to the number average particle diameter d50b of the hydrophobic solid particles B is greater than 100, it is possible to form the composite particles, but it is difficult to stably produce liquid-encapsulating particles.

The number average particle diameter d50a of the hydrophobic solid particles A is not particularly limited and may be appropriately selected depending on the intended purpose so long as the effect of the present disclosure can be obtained, and is preferably 0.1 micrometers or greater but 10 micrometers or less, and more preferably 0.5 micrometers or greater but 5 micrometers or less. When the number average particle diameter d50a of the hydrophobic solid particles A is 0.1 micrometers or greater but 10 micrometers or less, the amount of the hydrophobic solid particles A to be adsorbed to liquid droplets can be increased, making it possible to more stabilize liquid-encapsulating particles described below.

The number average particle diameter d50b of the hydrophobic solid particles B is not particularly limited and may be appropriately selected depending on the intended purpose so long as the effect of the present disclosure can be achieved, and for example, is preferably 0.01 micrometers or greater but 0.5 micrometers or less and more preferably 0.01 micrometers or greater but 0.05 micrometers or less. When the number average particle diameter d50b of the hydrophobic solid particles B is 0.01 micrometers or greater but 0.5 micrometers or less, the amount of the hydrophobic solid particles B to be adsorbed to the hydrophobic solid particles A can be increased, making it possible to more stabilize liquid-encapsulating particles described below.

A coating ratio CR of the composite particles of the present disclosure expressed by Formula 1 below is 50% or higher but 500% or lower.

Formula 1

$$\text{Coating ratio } CR\ (\%) = \frac{\pi(d50b/2)^2}{4\pi(d50a/2+d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

The mass (g) and the volume (cubic micrometer) may be values per unit particle, but may be values per bulk so long as the mass and the volume of the composite particles used can be obtained on the same basis as the values per bulk. The volume of each particle may be the average of the volumes of particles used, or may be the volume of a true sphere calculated assuming that the particle is a true sphere having an obtained number average particle diameter as the diameter.

The coating ratio means an abundance ratio of the hydrophobic solid particle B present over the surface of the hydrophobic solid particle A.

The coating ratio CR is obtained in the manner described below.

When the composite particles are assumed to be true spheres (the hydrophobic solid particles A and B are also true spheres), the surface area ($4\pi(d50a/2+d50b/2)^2$) of the composite particles is calculated, where (d50a/2+d50b/2), which is the sum of the quotients obtained by dividing the number average particle diameter d50a of the hydrophobic solid particles A and the number average particle diameter d50b of the hydrophobic solid particles B each by 2, is the radius of the composite particles.

The area over which hydrophobic solid particles B coat the surface of the hydrophobic solid particle A is obtained by multiplying the area of a cross-section Sb of the hydrophobic solid particle B by the number of hydrophobic solid particles B coating one hydrophobic solid particle A, where the cross-section Sb is orthogonal to the line segment connecting the center of the one hydrophobic solid particle A with the center of the hydrophobic solid particle B and includes the center of the hydrophobic solid particle B. The area of the cross-section Sb is expressed as $\pi(d50b/2)^2$, using the number average particle diameter d50b of the hydrophobic solid particles B. The number of hydrophobic solid particles B coating one hydrophobic solid particle A can be expressed as $\{Xb(g/\mu m^3)/Zb(g/\mu m^3)\}/\{Xa(g)/Ya(g/\mu m)/Za(g/\mu m^3)\}$, using the mass Xa, the density Ya, and the volume Za of the hydrophobic solid particle A and the mass Xb, the density Yb, and the volume Zb of the hydrophobic solid particle B.

Figure 1B:
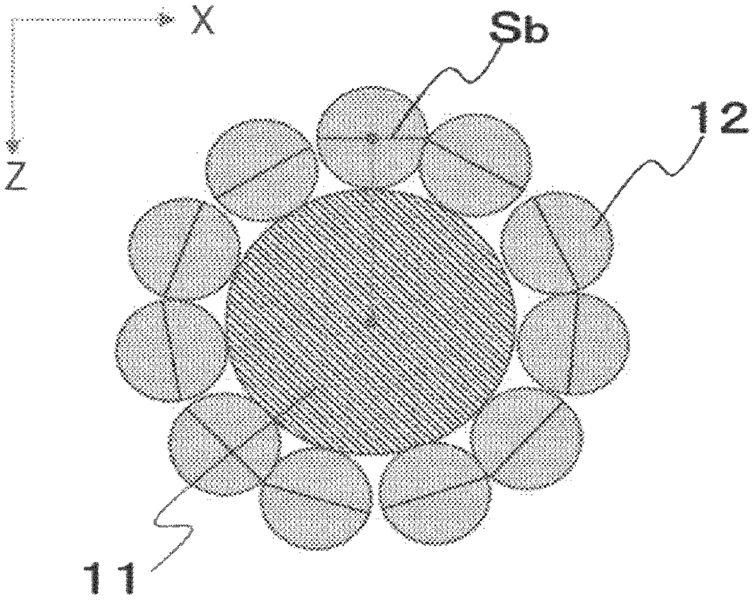
FIG. 1B is an exemplary view illustrating an example of a cross-section taken in the X-Z plane of FIG. 1A.

FIG. 1A is an exemplary view illustrating an example of the composite particles of the present disclosure. FIG. 1B is an exemplary view illustrating an example of a cross-section taken in the X-Z plane of FIG. 1A.

As illustrated in FIG. 1A, the composite particles 10 of the present disclosure include a hydrophobic solid particle A11 and hydrophobic solid particles B12. The hydrophobic solid particles B12 coat the surface of the hydrophobic solid particle A11. The coating ratio CR is calculated as the ratio of the area occupied by the hydrophobic solid particles B12 to the surface area of the composite particle 10, where the surface area of the composite particle 10 is calculated based on the number average particle diameter d50a of the hydrophobic solid particles A11 and the number average particle diameter d50b of the hydrophobic solid particles B12. The area occupied by the hydrophobic solid particles B12 is obtained by multiplying the area of a cross-section Sb of the hydrophobic solid particle B12 by the number of hydrophobic solid particles B coating one hydrophobic solid particle A11, where the cross-section Sb is orthogonal to the line segment connecting the center of the one hydrophobic solid particle A11 with the center of the hydrophobic solid particle B12 and includes the center of the hydrophobic solid particle B12 as illustrated in FIG. 1B.

The coating ratio CR is 50% or higher but 500% or lower, and preferably 100% or higher but 200% or lower. When the coating ratio CR is 50% or higher but 500% or lower, liquid-encapsulating particles excellent in coalescing suppressibility and durability against external forces can be formed. When the coating ratio CR is lower than 50%, the hydrophobic solid particles A dominantly contact the water or the solution, making it difficult to obtain the effect of suppressing coalescing. When the coating ratio CR is higher than 500%, the hydrophobic solid particles B aggregate and accumulate over the surface of the hydrophobic solid particles A and dominantly contact the water or the solution, making it difficult to obtain the effect of suppressing coalescing.

The material of the hydrophobic solid particles A is not particularly limited and may be appropriately selected depending on the intended purpose so long as the material has the contact angle CAa of 110 degrees or greater but 180 degrees or less with the water. Examples of the material of the hydrophobic solid particles A include organic materials and inorganic materials.

Examples of the organic materials include polymer materials.

Examples of the polymer materials include resins.

Examples of the resins include fluororesins, silicone resins, cellulose, and copolymers containing at least one of these resins.

Examples of the fluororesins include polytetrafluoroethylene (PTFE), perfluoroalkoxyalkane (PFA), perfluoroethylene propene copolymers (FEP), ethylene tetrafluoroethylene copolymers (ETFE), polyvinylidene fluoride (PVDF), polychlorotrifluoroethylene (PCTFE), and ethylene chlorotrifluoroethylene copolymers (ECTFE).

Examples of the silicone resins include methyl silicone resins and urethane-modified silicone resins.

Examples of the inorganic materials include silica and calcium carbonate.

Examples of the silica include fumed silica and silica spherical particles (QSG series: available from Shin-Etsu Chemical Co., Ltd.).

A hydrophobizing treatment may be applied to the surfaces of the organic materials and the inorganic materials. Any of the organic materials and the inorganic materials that do not have hydrophobicity as a material property may be used with hydrophobicity imparted to the surfaces by the hydrophobizing treatment.

Examples of the organic materials to which the hydrophobizing treatment is applied include hydrophobized starch. Examples of the hydrophobized starch include octenylsuccinic acid corn starch ester aluminum (product name: OCTIE, available from Nippon Starch Chemical Co., Ltd.).

It is possible to confirm that the organic material is hydrophobized, by measuring the contact angle. It is possible to confirm that the organic material is hydrophobized, by measuring the contact angle of a compression-molded (e.g., hot-pressed) sample obtained by the method described above and seeing to it that the contact angle is 90 degrees or greater but 180 degrees or less.

Examples of the inorganic materials to which the hydrophobizing treatment is applied include stearic acid-treated calcium carbonate. Examples of the stearic acid-treated calcium carbonate include a product obtained by mixing calcium carbonate (100 g) with stearic acid (10 g) and methanol (500 ml), evaporating methanol at reduced pressure, and heating and drying the resultant at 50 degrees C.

It is possible to confirm that the inorganic material is hydrophobized, by measuring the contact angle. For example, when the hydrophobizing treatment is a treatment with stearic acid, it is possible to confirm that the inorganic material is treated with stearic acid, by measuring the contact angle of a compression-molded (e.g., hot-pressed) sample and seeing to it that the contact angle is 90 degrees or greater or 180 degrees or less.

The material of the hydrophobic solid particles B is not particularly limited and may be appropriately selected depending on the intended purpose so long as the material has the contact angle CAb of 110 degrees or greater but 180 degrees or less with the water. Examples of the material of the hydrophobic solid particles B include organic materials and inorganic materials.

Examples of the organic materials include polymer materials.

Examples of the polymer materials include resins.

Examples of the resins include fluororesins, silicone resins, cellulose, and copolymers containing at least one of these resins.

Examples of the fluororesins include polytetrafluoroethylene (PTFE), perfluoroalkoxyalkane (PFA), perfluoroethylene propene copolymers (FEP), ethylene tetrafluoroethylene copolymers (ETFE), polyvinylidene fluoride (PVDF), polychlorotrifluoroethylene (PCTFE), and ethylene chlorotrifluoroethylene copolymers (ECTFE).

Examples of the silicone resins include methyl silicone resins and urethane-modified silicone resins.

Examples of the inorganic materials include silica and calcium carbonate.

Examples of the silica include fumed silica and silica spherical particles (QSG series: available from Shin-Etsu Chemical Co., Ltd.).

A hydrophobizing treatment may be applied to the surfaces of the organic materials and the inorganic materials. Any of the organic materials and the inorganic materials that do not have hydrophobicity as a material property may be used with hydrophobicity imparted to the surfaces by the hydrophobizing treatment.

Examples of the organic materials to which the hydrophobizing treatment is applied include hydrophobized starch. Examples of the hydrophobized starch include octenylsuccinic acid corn starch ester aluminum (product name: OCTIE, available from Nippon Starch Chemical Co., Ltd.).

It is possible to confirm that the organic material is hydrophobized, by measuring the contact angle. It is possible to confirm that the organic material is hydrophobized, by measuring the contact angle of a compression-molded (e.g., hot-pressed) sample obtained by the method described above and seeing to it that the contact angle is 100 degrees or greater.

Examples of the inorganic materials to which the hydrophobizing treatment is applied include stearic acid-treated calcium carbonate. Examples of the stearic acid-treated calcium carbonate include a product obtained by mixing calcium carbonate (100 g) with stearic acid (10 g) and methanol (500 ml), evaporating methanol at reduced pressure, and heating and drying the resultant at 50 degrees C.

It is possible to confirm that the inorganic material is hydrophobized, by measuring the contact angle. For example, when the hydrophobizing treatment is a treatment with stearic acid, it is possible to confirm that the inorganic material is treated with stearic acid, by measuring the contact angle of a compression-molded (e.g., hot-pressed) sample and seeing to it that the contact angle is 90 degrees or greater but 180 degrees or less.

The material of the hydrophobic solid particles B may be the same as or different from the material of the hydrophobic solid particles A so long as the above-described relationship between the hydrophobic solid particles A and the hydrophobic solid particles B according to the present disclosure is satisfied. It is preferable that at least either the hydrophobic solid particle A or the hydrophobic solid particle B be formed of at least one selected from fluororesins, silica, stearic acid-treated calcium carbonate, and hydrophobized starch.

The shape of the hydrophobic solid particles A and the hydrophobic solid particles B is not particularly limited and may be appropriately selected depending on the intended purpose so long as the shape has a structure that can achieve the effect of the present disclosure. Examples of the shape include spherical shapes, true-spherical shapes, flat shapes, acicular shapes, columnar shapes, indefinite shapes, and rectangular parallelepiped shapes.

The structure of the hydrophobic solid particles A and the hydrophobic solid particles B is not particularly limited and may be appropriately selected depending on the intended purpose so long as the structure can achieve the effect of the present disclosure. Examples of the structure include porous structures, hollow structures, and layered structures.

<Other Components>

The other components are not particularly limited and may be appropriately selected depending on the intended purpose. Examples of the other components include hydrophobic solid particles other than the hydrophobic solid particles A and the hydrophobic solid particles B that constitute the composite particles, and additives.

The hydrophobic solid particles other than the hydrophobic solid particles A and the hydrophobic solid particles B that constitute the composite particles are not particularly limited and may be appropriately selected depending on the intended purpose so long as the hydrophobic solid particles are hydrophobic solid particles other than the hydrophobic solid particles A and the hydrophobic solid particles B that constitute the composite particles.

The additives are not particularly limited and may be appropriately selected depending on the intended purpose so long as the additives can achieve the effect of the present disclosure. Examples of the additives include zinc stearate.

[Method for Producing Composite Particles]

The method for producing the composite particles of the present disclosure can obtain the composite particles by feeding the hydrophobic solid particles A and the hydrophobic solid particles B to a mixer under an inert gas and stirring the hydrophobic solid particles A and the hydrophobic solid particles B at 10 rpm for 12 hours.

As the method for analyzing the conditions of the composite particles, for example, a procured powder material may be subjected to dispersion treatment with addition of alcohol (for example, ethanol and isopropanol) to be separated into solid particles A and B, and then isolated by filtration, to measure the mass (g), density (g/cubic micrometer), and volume (cubic micrometer) of the solid particles A and the solid particles B. Subsequently, an image of each of the solid particles A and B isolated is taken with a scanning electron microscope, and the average of longest diameters of ten particles arbitrarily selected from the taken electron microscopic image may be calculated as the number average particle diameter of each. For the contact angles CAa and CAb, a plate-shaped body obtained by hot-pressing the material constituting the solid particles A or B isolated or a plate-shaped body obtained by casting a dispersion liquid of the solid particles A or B over a substrate by a casting method may be used as the sample to be measured, and the angle formed between water and the smooth surface when the water is located in an amount of 10 microliters over the sample with a microsyringe may be measured as the contact angle CAa or CAb with the water. With the water changed to the solution, the measuring method described above can be used as the method for measuring the contact angles CALa and CALb with the solution. The hot-pressing and the casting method are the same as the methods described above.

The mass (g) of the solid particles A and the solid particles B is measured with a precision balance.

The density (g/cubic micrometer) of the solid particles A and the solid particles B is a true density measurement and is measured with a Gay-Lussac type specific gravity bottle (a pycnometer method). As the density (g/cubic micrometer) of the solid particles A and the solid particles B, catalog values or literature values of the solid particles used may be used.

The volume (cubic micrometer) of the solid particles A and the solid particles B is calculated from the number average particle diameter.

(Liquid-Encapsulating Particles)

Liquid-encapsulating particles of the present disclosure include a liquid droplet, and composite particles including a hydrophobic solid particle A and a hydrophobic solid particle B over the surface of the hydrophobic solid particle A. The hydrophobic solid particle A has a contact angle CAa of 110 degrees or greater but 180 degrees or less with water. The hydrophobic solid particle B has a contact angle CAb of 110 degrees or greater but 180 degrees or less with water. The ratio (d50a/d50b) of the number average particle diameter d50a of the hydrophobic solid particle A to the number average particle diameter d50b of the hydrophobic solid particle B is 10 or greater but 100 or less. The coating ratio CR of the composite particles expressed by Formula 1 below is 50% or higher but 500% or lower. The surface of the liquid droplet is coated with the composite particles. The liquid-encapsulating particles further contain other components as needed.

Formula 1

$$\text{Coating ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The liquid-encapsulating particles of the present disclosure include a liquid droplet formed of a solution containing water in an amount of 15% by mass or greater, and composite particles. In the composite particles, the hydrophobic solid particle A has a contact angle CALa of 100 degrees or greater but 180 degrees or less with the solution, the hydrophobic solid particle B has a contact angle CALb of 100 degrees or greater but 180 degrees or less with the solution, the ratio (d50a/d50b) of the number average particle diameter d50a of the hydrophobic solid particle A to the number average particle diameter d50b of the hydrophobic solid particle B is 10 or greater but 100 or less, and the coating ratio CR of the composite particles expressed by Formula 1 below is 50% or higher but 500% or lower. The surface of the liquid droplet is coated with the composite particles. The liquid-encapsulating particles further contain other components as needed.

Formula 1

$$\text{Coating ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The liquid-encapsulating particles of the present disclosure refer to particles that are in a state that the surface of the liquid droplet is coated with the composite particles.

In the present disclosure, "the state that the surface of the liquid droplet is coated with the composite particles" is not particularly limited so long as the surface is coated enough to enable the effect of the present disclosure to be achieved, and the surface may be completely coated or may be partially coated.

—Composite Particles—

The composite particles are the same as the composite particles of the present disclosure.

—Liquid Droplet—

The liquid droplet is one selected from the group consisting of water and a solution containing water in an amount of 15% by mass or greater, and further contains other components as needed.

The solution is not particularly limited and may be appropriately selected depending on the intended purpose so long as the solution contains water in an amount of 15% by mass or greater. Examples of the solution include saline, a cell culture medium, and a glucose solution. Other substances that may be contained are not particularly limited and may be appropriately selected depending on the intended purpose. Examples of the substances include a water-soluble compound, a water-insoluble compound, a food additive, and a physiologically active substance.

Examples of the water-soluble compound include glucose, ascorbic acid, Japanese Pharmacopoeia honey, 1-ethyl-3-methyl imidazolium trifluoromethane sulfonate ([EMIM][$CF_3SO_3$]), 1-butyl-3-methyl imidazolium trifluoromethane sulfonate ([BMIM][$CF_3SO_3$]), (1-butyl-3-methyl imidazolium=chloride ([BMIM][Cl]), glycerin, polyglycerin, and lactose.

Examples of the water-insoluble compound include inorganic fillers such as titanium oxide, activated carbon, zeolite, and silica.

Examples of the food additive include antioxidants such as L-sodium ascorbate, and a fungicide.

Examples of the physiologically active substance include vitamins such as vitamin B1 and folic acid, and amino acids such as arginine and alanine.

—Other Components—

The other components are not particularly limited and may be appropriately selected depending on the intended purpose. Examples of the other components include a food additive and a physiologically active substance.

Examples of the food additive include antioxidants such as L-sodium ascorbate, and a fungicide.

Examples of the physiologically active substance include vitamins such as vitamin B1 and folic acid, and amino acids such as arginine and alanine.

The number average particle d50c of the liquid-encapsulating particles of the present disclosure is preferably 15 micrometers or greater but 2.5 mm or less, and more preferably 15 micrometers or greater but 1.0 mm or less. When the number average particle diameter d50c of the liquid-encapsulating particles is 15 micrometers or greater, the liquid-encapsulating particles can be suppressed from drying during production of the liquid droplets, making it possible to efficiently produce the liquid-encapsulating particles. When the number average particle diameter d50c of the liquid-encapsulating particles is 2.5 mm or less, spontaneous coalescing of the liquid-encapsulating particles and explosion of the liquid-encapsulating particles under the influence of the gravity can be suppressed.

The method for measuring the number average particle diameter d50c of the liquid-encapsulating particles is not particularly limited and may be appropriately selected depending on the intended purpose. Examples of the method include a method of observing the liquid-encapsulating particles with an optical microscope, measuring the longest diameters of arbitrary ten particles, and averaging the measured values.

Examples of the method for analyzing the components of the liquid droplet contained in the liquid-encapsulating particles include a method of exposing the liquid-encapsulating particles to ethanol vapor, separating the liquid-encapsulating particles into the liquid (liquid droplet) and the composite particles by filtration, and analyzing the liquid. The method for analyzing the liquid is not particularly limited and may be appropriately selected depending on the intended purpose. Examples of the method include liquid chromatography.

(Composite Particles for Forming Liquid-Encapsulating Particles)

The composite particles for forming liquid-encapsulating particles of the present disclosure are formed of the composite particles of the present disclosure, and include other components as needed.

The composite particles for forming liquid-encapsulating particles of the present disclosure are the same as the composite particles of the present disclosure.

For example, the composite particles for forming liquid-encapsulating particles of the present disclosure can be suitably used for the liquid-encapsulating particles of the present disclosure exclusively.

(Method for Producing Liquid-Encapsulating Particles and Apparatus for Producing Liquid-Encapsulating Particles)

A method for producing liquid-encapsulating particles of the present disclosure includes a liquid droplet forming step of forming a liquid droplet from a liquid, and a surface coating step of coating the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The method for producing liquid-encapsulating particles further includes other steps as needed.

Formula 1

$$\text{Coating ratio } CR\ (\%) = \frac{\pi(d50b/2)^2}{4\pi(d50a/2 + d50b/2)^2} \times \frac{\{X_b(g)/Y_b(g/\mu m^3)/Z_b(\mu m^3)\}}{\{X_a(g)/Y_a(g/\mu m^3)/Z_a(\mu m^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

A method for producing liquid-encapsulating particles of the present disclosure includes a liquid droplet forming step of forming a liquid droplet from a solution containing water in an amount of 15% by mass or greater, and a surface coating step of coating the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The method for producing liquid-encapsulating particles further includes other steps as needed.

Formula 1

$$\text{Coating ratio } CR\ (\%) = \frac{\pi(d50b/2)^2}{4\pi(d50a/2 + d50b/2)^2} \times \frac{\{X_b(g)/Y_b(g/\mu m^3)/Z_b(\mu m^3)\}}{\{X_a(g)/Y_a(g/\mu m^3)/Z_a(\mu m^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

An apparatus for producing liquid-encapsulating particles of the present disclosure includes a liquid droplet forming unit configured to form a liquid droplet from a liquid, and a surface coating unit configured to coat the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The apparatus for producing liquid-encapsulating particles further includes other units as needed.

Formula 1

$$\text{Coating ratio } CR\ (\%) = \frac{\pi(d50b/2)^2}{4\pi(d50a/2 + d50b/2)^2} \times \frac{\{X_b(g)/Y_b(g/\mu m^3)/Z_b(\mu m^3)\}}{\{X_a(g)/Y_a(g/\mu m^3)/Z_a(\mu m^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

An apparatus for producing liquid-encapsulating particles of the present disclosure includes a liquid droplet forming unit configured to form a liquid droplet from a solution containing water in an amount of 15% by mass or greater, and a surface coating unit configured to coat the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The apparatus for producing liquid-encapsulating particles further includes other units as needed.

Formula 1

$$\text{Coating Ratio } CR\ (\%) = \frac{\pi(d50b/2)^2}{4\pi(d50a/2 + d50b/2)^2} \times \frac{\{X_b(g)/Y_b(g/\mu m^3)/Z_b(\mu m^3)\}}{\{X_a(g)/Y_a(g/\mu m^3)/Z_a(\mu m^3)\}} \times 100$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The method for producing liquid-encapsulating particles of the present disclosure can be suitably performed using the apparatus for producing liquid-encapsulating particles. The liquid droplet forming step can be suitably performed by the liquid droplet forming unit. The surface coating step can be suitably performed by the surface coating unit.

<Liquid Droplet Forming Step and Liquid Droplet Forming Unit>

The liquid droplet forming step is a step of forming a liquid droplet from a liquid.

The liquid droplet forming unit is a unit configured to form a liquid droplet from a liquid.

The liquid droplet forming step can be suitably performed by the liquid droplet forming unit.

The liquid is not particularly limited and may be appropriately selected depending on the intended purpose. Examples of the liquid include water and a solution containing water in an amount of 15% by mass or greater.

The liquid is not particularly limited and may be appropriately selected depending on the intended purpose so long as the liquid contains water in an amount of 15% by mass or greater. Examples of the liquid include saline, a cell culture medium, and a glucose solution. Other substances that may be contained are not particularly limited and may be appropriately selected depending on the intended purpose. Examples of the substances include a water-soluble compound, a water-insoluble compound, a food additive, and a physiologically active substance.

Examples of the water-soluble compound include glucose, ascorbic acid, Japanese Pharmacopoeia honey, 1-ethyl-3-methyl imidazolium trifluoromethane sulfonate ([EMIM][$CF_3SO_3$]), 1-butyl-3-methyl imidazolium trifluoromethane sulfonate ([BMIM][$CF_3SO_3$]), (1-butyl-3-methyl imidazolium=chloride ([BMIM][Cl]), glycerin, polyglycerin, and lactose.

Examples of the water-insoluble compound include inorganic fillers such as titanium oxide, activated carbon, zeolite, and silica.

Examples of the food additive include antioxidants such as L-sodium ascorbate, and a fungicide.

Examples of the physiologically active substance include: vitamins such as vitamin B1 and folic acid, and amino acids such as arginine and alanine.

A known liquid droplet forming unit can be used as the liquid droplet forming unit. The liquid droplet forming unit is not particularly limited and may be appropriately selected depending on the intended purpose so long as the liquid droplet forming unit can form a liquid droplet from a liquid. Examples of the liquid droplet forming unit include an inkjet type, a dispenser type, and a spray drying type. Among these liquid droplet forming units, the dispenser type is preferable because the dispenser type is versatile with a broad range of liquid properties that can be formed into a liquid droplet and can control the size of a liquid droplet by the size of the pore diameter of the head and the pressure for pushing out the liquid filled.

<Surface Coating Step and Surface Coating Unit>

The surface coating step is a step of coating the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower.

$$\text{Coating Ratio } CR\ (\%) = \frac{\pi(d50b/2)^2}{4\pi(d50a/2 + d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The surface coating unit is a unit configured to coat the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower.

$$\text{Coating Ratio } CR\ (\%) = \frac{\pi(d50b/2)^2}{4\pi(d50a/2 + d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The surface coating step is a step of coating the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower.

$$\text{Coating Ratio } CR\ (\%) = \frac{\pi(d50b/2)^2}{4\pi(d50a/2 + d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The surface coating unit is a unit configured to coat the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower.

$$\text{Coating Ratio } CR\ (\%) = \frac{\pi(d50b/2)^2}{4\pi(d50a/2 + d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particle A, Xb represents the mass (g) of the hydrophobic solid particle B, Ya represents the density (g/cubic micrometer) of the hydrophobic solid particle A, Yb represents the density (g/cubic micrometer) of the hydrophobic solid particle B, Za represents the volume (cubic micrometer) of the hydrophobic solid particle A, and Zb represents the volume (cubic micrometer) of the hydrophobic solid particle B.

The surface coating step can be suitably performed by the surface coating unit.

In the present disclosure, "surface coating" means that the surface of a liquid droplet is coated enough to enable the effect of the present disclosure to be achieved. Surface coating is not particularly limited and may be complete coating of a liquid droplet or may be partial coating of a liquid droplet.

—Composite Particles—

The composite particles are the same as the composite particles of the present disclosure.

The method for coating the surface of the liquid droplet is not particularly limited and may be appropriately selected depending on the intended purpose so long as the method can bring the liquid droplet and the composite particles into contact with each other. Examples of the method include a method of spraying the composite particles to the liquid droplet that is flying, and a method of locating a liquid droplet in a container in which the composite particles are densely laid. Of these methods, the method of locating a liquid droplet in a container in which the composite particles are densely laid is preferable in terms of excellent ease of device control.

In the method of locating a liquid droplet in a container in which the composite particles are densely laid, after a liquid droplet is located in the container in which the composite particles are densely laid, it is preferable to add, for example, a step of shaking the container while supplying the composite particles into the container, and a step of inclining the container and rolling the liquid droplet, in order to coat the entire surface of the liquid droplet with the composite particles. These steps may be performed independently, or either step may be performed after the other step is performed.

As the unit configured to supply the composite particles into the container, a commercially available powder supplying apparatus may be used. The mechanism and the type of the powder supplying apparatus may be appropriately selected depending on the conditions of the composite particles.

<Other Steps and Other Units>

The other steps are not particularly limited and may be appropriately selected depending on the intended purpose. Examples of the other steps include a separating step and a collecting step.

The other units are not particularly limited and may be appropriately selected depending on the intended purpose. Examples of the other units include a separating unit and a collecting unit.

The other steps can be suitably performed by the other units. The separating step can be suitably performed by the separating unit. The collecting step can be suitably performed by the collecting unit.

<<Separating Step and Separating Unit>>

The separating step is a step of separating the liquid-encapsulating particles from the composite particles left unused for surface coating in the surface coating step.

The separating unit is a unit configured to separate the liquid-encapsulating particles from the composite particles left unused for surface coating in the surface coating step.

Examples of the method of separating the liquid-encapsulating particles from the composite particles left unused for surface coating in the surface coating step include a method of picking up the liquid-encapsulating particles, and a method of separating the mixture of the liquid-encapsulating particles and the composite particles utilizing the density difference and removing the composite particles. Of these methods, the method utilizing the density difference is preferable in terms of productivity.

Examples of the method of separating the mixture of the liquid-encapsulating particles and the composite particles utilizing the density difference and removing the composite particles include a method of passing the mixture through a push-pull dust chamber.

<<Collecting Step and Collecting Unit>>

The collecting step is a step of collecting the liquid-encapsulating particles separated.

The collecting unit is a unit configured to collect the liquid-encapsulating particles separated.

The method for collecting the liquid-encapsulating particles separated is not particularly limited and may be appropriately selected depending on the intended purpose. Examples of the method include a method of letting the liquid-encapsulating particles fall from the container to be collected into a collecting container. In order to alleviate the impact of falling, it is preferable to set the collecting container at a distance of within 200 mm from the container, and to incline the collecting container. It is preferable to hydrophobize the internal wall of the collecting container or to form the collecting container using a hydrophobic material.

(Biocatalyst-Containing Material)

A biocatalyst-containing material of the present disclosure contains a liquid droplet containing a biocatalyst, and composite particles coating the surface of the liquid droplet. The number average particle diameter d50c of the biocatalyst-containing material is 10 micrometers or greater but 1,000 micrometers or less.

Generally, substance producing processes using microorganisms that produce valuables are performed under strict management of culture fluids in large-sized culture tanks.

However, such culture systems need appropriate stirring and supply of gases such as oxygen. This makes the process and management complicated.

Moreover, there are cases where microorganisms that have died in the large-sized culture tanks also lead surrounding microorganisms to death. This makes substance production unsuccessful.

According to recent reports, liquid droplets are encapsulated in particles, and biocatalysts such as microorganisms are contained in the encapsulated liquid droplets, to culture the microorganisms in the liquid-encapsulating particles (for example, see Colloids and Surfaces B: Biointerfaces 106 (2013) 187-190).

Existing techniques for culturing, for example, microorganisms using liquid-encapsulating particles have used particles having a size of some millimeters or greater that makes durability (strength) low and coalescing likely to occur, leading to a problem that many particles cannot be handled in the same system. Another problem of the large size of the particles used is that stirring and gas supply for circulating liquids inside the particles is difficult.

Hence, the present inventor has studied a biocatalyst-containing material having a high valuable producing efficiency and an excellent durability against external forces, and obtained the following finding.

Existing techniques have been found to be unable to efficiently produce biocatalyst-containing liquid-encapsulating particles having a particle diameter of 10 micrometers or greater but 1,000 micrometers or less because such particles have a low durability (strength). Furthermore, although existing techniques have been able to produce particles having a particle diameter of less than 10 micrometers, it has been found that liquids tend to dry during production and adversely affect the internal biocatalysts, to make the valuable producing efficiency low. Moreover, although existing techniques have been able to produce particles having a particle diameter of greater than 2,000 micrometers, it has been found that the volume of the liquids encapsulated is so high that it is difficult to spread components (for example, oxygen) for enabling the biocatalysts to function inside the particles, to make the valuable producing efficiency low.

The biocatalyst-containing material of the present disclosure refers to a material that is in a state that the surface of the liquid droplet is coated with the composite particles.

In the present disclosure, "the state that the surface of the liquid droplet is coated with the composite particles" is not particularly limited so long as the surface is coated enough to enable the effect of the present disclosure to be achieved, and the surface may be completely coated or may be partially coated.

Therefore, in order to obtain particles having an excellent valuable producing efficiency and an excellent coalescing and durability, it has been found appropriate to distribute composite particles around a liquid droplet to adjust the size of the particle to 10 micrometers or greater but 1,000 micrometers or less. The valuable is not particularly limited and may be appropriately selected depending on the intended purpose so long as the valuable ca be produced with a biocatalyst. Examples of the valuable include ethanol, acetic acid, lactic acid, butyric acid, propionic acid, and formic acid.

The biocatalyst-containing material of the present disclosure has a high valuable producing efficiency and an excellent durability against external forces.

—Liquid Droplet—

The liquid droplet is not particularly limited and may be appropriately selected depending on the intended purpose so long as the liquid droplet contains a biocatalyst and is not a solution that inhibits reaction of the biocatalyst.

The solution is not particularly limited and may be appropriately selected depending on the intended purpose so long as the solution contains water in an amount of 15% by mass or greater. Examples of the liquid include saline, a cell culture medium, and a glucose solution. Other substances that may be contained are not particularly limited and may be appropriately selected depending on the intended purpose. Examples of the substances include a water-soluble compound, and a water-insoluble compound.

Examples of the water-soluble compound include glucose, ascorbic acid, Japanese Pharmacopoeia honey, 1-ethyl-3-methyl imidazolium trifluoromethane sulfonate ([EMIM][$CF_3SO_3$]), 1-butyl-3-methyl imidazolium trifluoromethane sulfonate ([BMIM][$CF_3SO_3$]), (1-butyl-3-methyl imidazolium=chloride ([BMIM][Cl]), glycerin, polyglycerin, and lactose.

Examples of the water-insoluble compound include inorganic fillers such as titanium oxide, activated carbon, zeolite, and silica.

Examples of the food additive include antioxidants such as L-sodium ascorbate, and a fungicide.

Examples of the physiologically active substance include vitamins such as vitamin B1 and folic acid, and amino acids such as arginine and alanine.

—Biocatalyst—

The biocatalyst is not particularly limited and may be appropriately selected depending on the intended purpose, so long as the biocatalyst is a living organism per se or a catalyst derived from a living organism and can change the reaction speed of a reaction of a substance transforming into a substance of a different kind.

Examples of the living organism per se include animal cells, plant cells, and microorganisms.

Examples of the catalyst derived from a living organism include enzymes.

—Composite Particles—

The composite particles include a hydrophobic solid particle A and a hydrophobic solid particle B, includes the hydrophobic solid particle B over the surface of the hydrophobic solid particle A, and further include other materials as needed.

The present inventor has found that liquid droplet-encapsulating particles (may be referred to as liquid marbles or liquid-encapsulating particles) produced only with particles having a large particle diameter have a small contact area between the particles coating the liquid droplets and the liquid droplets, to have the liquid droplets exposed at some positions, leading to a very poor strength against external forces and difficulty with improving durability.

The present inventor has also found that liquid-encapsulating particles produced only with particles having a small particle diameter have a better durability against external forces, but are easily deformable, leading to a problem that the liquid-encapsulating particles may coalesce with each other due to a capillary phenomenon.

Hence, the present inventor has found that use of two kinds of hydrophobic solid particles having a specific property and having different particle diameters (hydrophobic solid particles A having a greater particle diameter and hydrophobic solid particles B having a smaller particle diameter) makes it possible to suppress coalescing of liquid-encapsulating particles.

The present inventor has also found that composite particles in which the hydrophobic solid particles B are distributed over the surface of the hydrophobic solid particles A can suppress coalescing of liquid-encapsulating particles, can coat the surface of liquid droplets of various kinds of liquids, and can form liquid-encapsulating particles having an excellent durability.

—Hydrophobic Solid Particle A and Hydrophobic Solid Particle B—

The hydrophobic solid particle B is present over the surface of the hydrophobic solid particle A and coats the surface of the hydrophobic solid particle A. The hydrophobic solid particle B coating the surface of the hydrophobic solid particle A means that the hydrophobic solid particle B coats the surface of the hydrophobic solid particle A enough to enable the effect of the present disclosure to be achieved, and that the hydrophobic solid particle B coats the surface of the hydrophobic solid particle A in a manner to satisfy a coating ratio CR described below.

In the present disclosure, “the surface of the hydrophobic solid particle A” means the exposed surface of the hydrophobic solid particle A.

The hydrophobic solid particle A has a contact angle CAa of 110 degrees or greater but 180 degrees or less with water. The hydrophobic solid particle B has a contact angle CAb of 110 degrees or higher but 180 degrees or lower with water.

When the contact angles CAa and CAb with water are 110 degrees or higher but 180 degrees or lower, coalescing of the biocatalyst-containing material can be suppressed.

In the present disclosure, “hydrophobicity” means a contact angle CAa and a contact angle CAb of 90 degrees or greater but 180 degrees or less with water when measured by a method for measuring the contact angles described below.

With respect to a solution containing water in an amount of 15% by mass or greater, the hydrophobic solid particle A has a contact angle CALa of 100 degrees or greater but 180 degrees or lower with the solution, and the hydrophobic solid particle B has a contact angle CALb of 100 degrees or greater but 180 degrees or lower with the solution.

When the contact angles CALa and CALb of the hydrophobic solid particle A and the hydrophobic solid particle B with the solution are 100 degrees or greater but 180 degrees or lower, coalescing of solution-encapsulating particles can be suppressed.

As the method for measuring the contact angles CAa and CAb with water, a plate-shaped body obtained by hot-pressing the material constituting the hydrophobic solid particle A or B or a plate-shaped body obtained by casting a dispersion liquid of the material constituting the hydrophobic solid particle A or B over a substrate by a casting method is used as the sample to be measured, and the angle formed between the liquid surface of water and the surface of the plate-shaped body when the water is located in an amount of 10 microliters over the sample with a microsyringe is measured as the contact angle CAa or CAb with the water (according to a known contact angle measuring method (θ/2 method)). With the water changed to the solution, the measuring method described above can be used as the method for measuring the contact angles CALa and CALb with the solution.

The conditions of the hot-pressing when producing the plate-shaped body by hot-pressing the material constituting the hydrophobic solid particle A or B are as follows.

[Hot-Pressing Conditions]

Temperature: 200 degrees C.

Total pressure applied: 30 kN

Time: for 5 minutes from when the pressure reaches 30 kN

Operation: A powder of the sample (the material constituting the hydrophobic solid particle) is filled in a powder compacting die having an internal diameter of 10 mm and a depth of 20 mm until the height of the powder from the bottom reaches 10 mm, and set in a press machine (machine name: SA302 DESK-TOP TEST PRESS, available from Tester Sangyo Co., Ltd.). After it is confirmed that the die has reached a predetermined temperature (200 degrees C.), pressing is started up to a predetermined pressure (30 kN). The material is pressed for 5 minutes from when the pressure reaches the predetermined pressure. In this way, the sample is produced.

The plate-shaped body obtained by casting a dispersion liquid of the material constituting the hydrophobic solid particle A or B over a substrate by a casting method is obtained by the hot-pressing described above on a powder of the sample (the material constituting the hydrophobic solid particle) approximately uniformly sprinkled over PTFE (polytetrafluoroethylene, with an average thickness of 200 micrometers) that is punched to have a diameter of 10 mm and set on the powder compacting die in the production of the plate-shaped body by the hot-pressing of the material constituting the hydrophobic solid particle A or B.

The method for approximately uniformly sprinkling the powder of the sample (the material constituting the hydrophobic solid particle) is not particularly limited and may be approximately selected depending on the intended purpose. Examples of the method include a method of sprinkling a dry sample powder, and a method of sprinkling a sample dispersion liquid. A solvent used in the sample dispersion liquid is not particularly limited and may be appropriately selected depending on the intended purpose. Examples of the solvent include ethanol. When the sample dispersion liquid is used, it is easy to handle a sample having a low bulk density.

When using the materials constituting the hydrophobic solid particle A and the hydrophobic solid particle B of the composite particles as the samples to be measured, the materials of the hydrophobic solid particle A and the hydrophobic solid particle B may be identified by, for example, gas chromatography (GC-MS), nuclear magnetic resonance (NMR), and infrared spectroscopy (IR) to procure the materials and measure the contact angles CAa and CAb with the water using the procured materials, or the hydrophobic solid particle A and the hydrophobic solid particle B may be isolated from the composite particles to produce the plate-shaped body using the hydrophobic solid particle A or hydrophobic solid particle B isolated and measure the contact angles CAa and CAb with the water. With the water changed to the solution, the measuring method described above can be used as the method for measuring the contact angles CALa and CALb with the solution.

Examples of the method for isolating the hydrophobic solid particle A and the hydrophobic solid particle B from the composite particles include a method of filtrating a dispersion liquid of the composite particles obtained by adding an alcohol (for example, ethanol and isopropanol) to the composite particles. Of these alcohols, ethanol is preferable. Ethanol is preferable because of a high volatility that facilitates drying after filtration.

The ratio (d50a/d50b) of the number average particle diameter d50a of the hydrophobic solid particles A to the number average particle diameter d50b of the hydrophobic solid particles B is preferably 10 or greater but 100 or less.

The number average particle diameter d50a of the hydrophobic solid particles A and the number average particle diameter d50b of the hydrophobic solid particles B are each the average of longest diameters of ten particles arbitrarily selected from a scanning electron microscopic image of the hydrophobic solid particles A or the hydrophobic solid particles B isolated by the method described above and observed by bulk.

The ratio (d50a/d50b) of the number average particle diameter d50a of the hydrophobic solid particles A to the number average particle diameter d50b of the hydrophobic solid particles B is preferably 10 or greater but 100 or less, and more preferably 30 or greater but 50 or less. When the ratio (d50a/d50b) of the number average particle diameter d50a of the hydrophobic solid particles A to the number average particle diameter d50b of the hydrophobic solid particles B is 10 or greater but 100 or less, a biocatalyst-containing material excellent in coalescing suppressibility and durability against external forces can be formed. When the ratio (d50a/d50b) of the number average particle diameter d50a of the hydrophobic solid particles A to the number average particle diameter d50b of the hydrophobic solid particles B is less than 10, it is difficult to form the composite particles. When the ratio (d50a/d50b) of the number average particle diameter d50a of the hydrophobic solid particles A to the number average particle diameter d50b of the hydrophobic solid particles B is greater than 100, it is possible to form the composite particles, but it is difficult to stably produce the biocatalyst-containing material.

The number average particle diameter d50a of the hydrophobic solid particles A is not particularly limited and may be appropriately selected depending on the intended purpose so long as the effect of the present disclosure can be achieved, and is preferably 0.1 micrometers or greater but 10 micrometers or less, preferably 0.3 micrometers or greater but 5 micrometers or less, and more preferably 0.5 micrometers or greater but 1 micrometer or less. When the number average particle diameter d50a of the hydrophobic solid particles A is 0.1 micrometers or greater but 10 micrometers or less, the amount of the hydrophobic solid particles A to be adsorbed to the liquid droplets can be increased, making it possible to more stabilize the biocatalyst-containing material (liquid-encapsulating particles) to be produced.

The number average particle diameter d50b of the hydrophobic solid particles B is not particularly limited and may be appropriately selected depending on the intended purpose so long as the effect of the present disclosure can be achieved, and for example, is preferably 0.01 micrometers or greater but 0.5 micrometers or less and more preferably 0.01 micrometers or greater but 0.05 micrometers or less. When the number average particle diameter d50b of the hydrophobic solid particles B is 0.01 micrometers or greater but 0.5 micrometers or less, the amount of the hydrophobic solid particles B to be adsorbed to the hydrophobic solid particles A can be increased, making it possible to more stabilize the biocatalyst-containing material (liquid-encapsulating particles).

A coating ratio CR of the composite particles expressed by Formula 1 below is preferably 50% or higher but 500% or lower.

$$\text{Coating Ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100 \qquad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

The mass (g) and the volume (cubic micrometer) may be values per unit particle, but may be values per bulk so long as the mass and the volume of the composite particles used can be obtained on the same basis as the values per bulk. The volume of each particle may be the average of the volumes of particles used, or may be the volume of a true sphere calculated assuming that the particle is a true sphere having an obtained number average particle diameter as the diameter.

The coating ratio means an abundance ratio of the hydrophobic solid particle B present over the surface of the hydrophobic solid particle A.

The coating ratio CR is obtained in the manner described below.

When the composite particles are assumed to be true spheres (the hydrophobic solid particles A and B are also true spheres), the surface area ($4\pi(d50a/2+d50b/2)^2$) of the composite particles is calculated, where (d50a/2+d50b/2), which is the sum of the quotients obtained by dividing the number average particle diameter d50a of the hydrophobic solid particles A and the number average particle diameter d50b of the hydrophobic solid particles B each by 2, is the radius of the composite particles.

The area over which hydrophobic solid particles B coat the surface of the hydrophobic solid particle A is obtained by multiplying the area of a cross-section Sb of the hydrophobic solid particle B by the number of hydrophobic solid particles B coating one hydrophobic solid particle A, where the cross-section Sb is orthogonal to the line segment connecting the center of the one hydrophobic solid particle A with the center of the hydrophobic solid particle B and includes the center of the hydrophobic solid particle B. The area of the cross-section Sb is expressed as $\pi(d50b/2)^2$, using the number average particle diameter d50b of the hydrophobic solid particles B. The number of hydrophobic solid particles B coating one hydrophobic solid particle A can be expressed as $\{Xb(g)/Yb(g/\mu m^3)/Zb(g/\mu m^3)\}/\{Xa(g)/Ya(g/\mu m^3)/Za(g/\mu m^3)\}$, using the mass Xa, the density Ya, and the volume Za of the hydrophobic solid particle A and the mass Xb, the density Yb, and the volume Zb of the hydrophobic solid particle B.

FIG. 1A is an exemplary view illustrating an example of the composite particles of the present disclosure. FIG. 1B is an exemplary view illustrating an example of a cross-section taken in the X-Z plane of FIG. 1A.

As illustrated in FIG. 1A, the composite particles 10 of the present disclosure include a hydrophobic solid particle A11 and hydrophobic solid particles B12. The hydrophobic solid particles B12 coat the surface of the hydrophobic solid particle A11. The coating ratio CR is calculated as the ratio of the area occupied by the hydrophobic solid particles B12 to the surface area of the composite particle 10, where the surface area of the composite particle 10 is calculated based on the number average particle diameter d50a of the hydrophobic solid particles A11 and the number average particle diameter d50b of the hydrophobic solid particles B12. The area occupied by the hydrophobic solid particles B12 is obtained by multiplying the area of a cross-section Sb of the hydrophobic solid particle B12 by the number of hydrophobic solid particles B coating one hydrophobic solid particle A11, where the cross-section Sb is orthogonal to the line segment connecting the center of the one hydrophobic solid particle A11 with the center of the hydrophobic solid particle B12 and includes the center of the hydrophobic solid particle B12 as illustrated in FIG. 1B.

The coating ratio CR is preferably 50% or higher but 500% or lower, and more preferably 100% or higher but 200% or lower. When the coating ratio CR is 50% or higher but 500% or lower, a biocatalyst-containing material excellent in coalescing suppressibility and durability against external forces can be formed. When the coating ratio CR is lower than 50%, the hydrophobic solid particles A dominantly contact the water or the solution, making it difficult to obtain the effect of suppressing coalescing. When the coating ratio CR is higher than 500%, the hydrophobic solid particles B aggregate and accumulate over the surface of the hydrophobic solid particles A and dominantly contact the water or the solution, making it difficult to obtain the effect of suppressing coalescing.

The material of the hydrophobic solid particles A is not particularly limited and may be appropriately selected depending on the intended purpose so long as the material has the contact angle CAa of 110 degrees or greater but 180 degrees or less with the water. Examples of the material of the hydrophobic solid particles A include organic materials and inorganic materials.

Examples of the organic materials include polymer materials.

Examples of the polymer materials include resins.

Examples of the resins include fluororesins, silicone resins, cellulose, and copolymers containing at least one of these resins.

Examples of the fluororesins include polytetrafluoroethylene (PTFE), perfluoroalkoxyalkane (PFA), perfluoroethylene propene copolymers (FEP), ethylene tetrafluoroethylene copolymers (ETFE), polyvinylidene fluoride (PVDF), polychlorotrifluoroethylene (PCTFE), and ethylene chlorotrifluoroethylene copolymers (ECTFE).

Examples of the silicone resins include methyl silicone resins and urethane-modified silicone resins.

Examples of the inorganic materials include silica and calcium carbonate.

Examples of the silica include fumed silica spherical particles (QSG series: available from Shin-Etsu Chemical Co., Ltd.).

A hydrophobizing treatment may be applied to the surfaces of the organic materials and the inorganic materials. Any of the organic materials and the inorganic materials that do not have hydrophobicity as a material property may be used with hydrophobicity imparted to the surfaces by the hydrophobizing treatment.

Examples of the organic materials to which the hydrophobizing treatment is applied include hydrophobized starch. Examples of the hydrophobized starch include octenylsuccinic acid corn starch ester aluminum (product name: OCTIE, available from Nippon Starch Chemical Co., Ltd.).

It is possible to confirm that the organic material is hydrophobized, by measuring the contact angle. It is possible to confirm that the organic material is hydrophobized, by measuring the contact angle of a compression-molded (e.g., hot-pressed) sample obtained by the method described above and seeing to it that the contact angle is 90 degrees or greater 180 degrees or less.

Examples of the inorganic materials to which the hydrophobizing treatment is applied include stearic acid-treated calcium carbonate. Examples of the stearic acid-treated calcium carbonate include a product obtained by mixing calcium carbonate (100 g) with stearic acid (10 g) and methanol (500 ml), evaporating methanol at reduced pressure, and heating and drying the resultant at 50 degrees C.

It is possible to confirm that the inorganic material is hydrophobized, by measuring the contact angle. For example, when the hydrophobizing treatment is a treatment with stearic acid, it is possible to confirm that the inorganic material is treated with stearic acid, by measuring the contact angle of a compression-molded (e.g., hot-pressed) sample and seeing to it that the contact angle is 90 degrees or greater but 180 degrees or less.

The material of the hydrophobic solid particles B is not particularly limited and may be appropriately selected depending on the intended purpose so long as the material has the contact angle CAb of 110 degrees or greater but 180 degrees or less with the water. Examples of the material of the hydrophobic solid particles B include organic materials and inorganic materials.

Examples of the organic materials include polymer materials.

Examples of the polymer materials include resins.

Examples of the resins include fluororesins, silicone resins, cellulose, and copolymers containing at least one of these resins.

Examples of the fluororesins include polytetrafluoroethylene (PTFE), perfluoroalkoxyalkane (PFA), perfluoroethylene propene copolymers (FEP), ethylene tetrafluoroethylene copolymers (ETFE), polyvinylidene fluoride (PVDF), polychlorotrifluoroethylene (PCTFE), and ethylene chlorotrifluoroethylene copolymers (ECTFE).

Examples of the silicone resins include methyl silicone resins and urethane-modified silicone resins.

Examples of the inorganic materials include silica and calcium carbonate.

Examples of the silica include fumed silica spherical particles (QSG series: available from Shin-Etsu Chemical Co., Ltd.).

It is possible to confirm that the organic material is hydrophobized, by measuring the contact angle. It is possible to confirm that the organic material is hydrophobized, by measuring the contact angle of a compression-molded (e.g., hot-pressed) sample obtained by the method described above and seeing to it that the contact angle is 90 degrees or greater but 180 degrees or less.

Examples of the inorganic materials to which the hydrophobizing treatment is applied include stearic acid-treated calcium carbonate. Examples of the stearic acid-treated calcium carbonate include a product obtained by mixing calcium carbonate (100 g) with stearic acid (10 g) and methanol (500 ml), evaporating methanol at reduced pressure, and heating and drying the resultant at 50 degrees C.

It is possible to confirm that the inorganic material is hydrophobized, by measuring the contact angle. For example, when the hydrophobizing treatment is a treatment with stearic acid, it is possible to confirm that the inorganic material is treated with stearic acid, by measuring the contact angle of a compression-molded (e.g., hot-pressed) sample and seeing to it that the contact angle is 90 degrees or greater but 180 degrees or less.

The material of the hydrophobic solid particles B may be the same as or different from the material of the hydrophobic solid particles A so long as the above-described relationship between the hydrophobic solid particles A and the hydrophobic solid particles B according to the present disclosure is satisfied. It is preferable that at least either the hydrophobic solid particle A or the hydrophobic solid particle B be formed of at least one selected from fluororesins, silica, stearic acid-treated calcium carbonate, and hydrophobized starch.

The shape of the hydrophobic solid particles A and the hydrophobic solid particles B is not particularly limited and may be appropriately selected depending on the intended purpose so long as the shape has a structure that can achieve the effect of the present disclosure. Examples of the shape include spherical shapes, true-spherical shapes, flat shapes, acicular shapes, columnar shapes, indefinite shapes, and rectangular parallelepiped shapes.

The structure of the hydrophobic solid particles A and the hydrophobic solid particles B is not particularly limited and may be appropriately selected depending on the intended purpose so long as the structure can achieve the effect of the present disclosure. Examples of the structure include porous structures, hollow structures, and layered structures.

<Other Components>

The other components are not particularly limited and may be appropriately selected depending on the intended purpose. Examples of the other components include hydrophobic solid particles other than the hydrophobic solid particles A and the hydrophobic solid particles B that constitute the composite particles, and additives.

The hydrophobic solid particles other than the hydrophobic solid particles A and the hydrophobic solid particles B that constitute the composite particles are not particularly limited and may be appropriately selected so long as the hydrophobic solid particles are hydrophobic solid particles other than the hydrophobic solid particles A and the hydrophobic solid particles B that constitute the composite particles.

The additives are not particularly limited and may be appropriately selected depending on the intended purpose so long as the additives can achieve the effect of the present disclosure. Examples of the additives include zinc stearate.

[Method for Producing Composite Particles]

The method for producing composite particles is the same as the method for producing composite particles of the present disclosure.

The method for analyzing the conditions of the composite particles is the same as the method described in the method for producing composite particles of the present disclosure.

The number average particle d50c of the biocatalyst-containing material is 10 micrometers or greater but 1,000 micrometers or less, preferably 15 micrometers or greater but 1,000 micrometers or less, and more preferably 500 micrometers or greater but 800 micrometers or less. When the number average particle diameter d50c of the biocatalyst-containing material is 10 micrometers or greater, the biocatalyst-containing material can be suppressed from drying during production of the liquid droplets, making it possible to efficiently produce the biocatalyst-containing material. When the number average particle diameter d50c of the biocatalyst-containing material is 1,000 micrometers or less, spontaneous coalescing of particles of the biocatalyst-containing material and explosion of the biocatalyst-containing material under the influence of the gravity can be suppressed.

The number average particle diameter d50c of the biocatalyst-containing material is obtained by observing the biocatalyst-containing material with an optical microscope, measuring the longest diameters of arbitrary ten particles, and averaging the measured values.

Examples of the method for analyzing the components of the liquid droplet contained in the biocatalyst-containing material (liquid-encapsulating particles) include a method of exposing the liquid-encapsulating particles to ethanol vapor, separating the liquid-encapsulating particles into the liquid (liquid droplet) and the composite particles by filtration, and analyzing the liquid. The method for analyzing the liquid is not particularly limited and may be appropriately selected depending on the intended purpose. Examples of the method include liquid chromatography.

(Biocatalyst-Containing Material Producing Method and Biocatalyst-Containing Material Producing Apparatus)

A biocatalyst-containing material producing method of the present disclosure includes a liquid droplet forming step of forming a liquid droplet from a liquid containing a biocatalyst, and a surface coating step of coating the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The biocatalyst-containing material producing method further includes other steps as needed.

$$\text{Coating Ratio } CR\ (\%) = \frac{\pi(d50b/2)^2}{4\pi(d50a/2 + d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

A biocatalyst-containing material producing apparatus of the present disclosure includes a liquid droplet forming unit configured to form a liquid droplet from a liquid containing a biocatalyst, and a surface coating unit configured to coat the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The biocatalyst-containing material producing apparatus further includes other units as needed.

$$\text{Coating Ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

A biocatalyst-containing material producing method of the present disclosure in another embodiment includes a liquid droplet forming step of forming a liquid droplet from a solution containing a biocatalyst and water in an amount of 15% by mass or greater, and a surface coating step of coating the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The biocatalyst-containing material producing method further includes other steps as needed.

$$\text{Coating Ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

A biocatalyst-containing material producing apparatus of the present disclosure in another embodiment includes a liquid droplet forming unit configured to form a liquid droplet from a solution containing a biocatalyst and water in an amount of 15% by mass or greater, and a surface coating unit configured to coat the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower. The biocatalyst-containing material producing apparatus further includes other units as needed.

$$\text{Coating Ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

The biocatalyst-containing material producing method of the present disclosure can be suitably performed using the biocatalyst-containing material producing apparatus. The liquid droplet forming step can be suitably performed by the liquid droplet forming unit. The surface coating step can be suitably performed by the surface coating unit.

<Liquid Droplet Forming Step and Liquid Droplet Forming Unit>

The liquid droplet forming step is a step of forming a liquid droplet from a liquid.

The liquid droplet forming unit is a unit configured to form a liquid droplet from a liquid.

The liquid droplet forming step in another embodiment is a step of forming a liquid droplet from a solution containing the biocatalyst and water in an amount of 15% by mass or greater.

The liquid droplet forming unit in another embodiment is a unit configured to form a liquid droplet from a solution containing the biocatalyst and water in an amount of 15% by mass or greater.

The liquid droplet forming step can be suitably performed by the liquid droplet forming unit.

The liquid is the same as the solution used in the biocatalyst-containing material of the present disclosure.

A known liquid droplet forming unit can be used as the liquid droplet forming unit. The liquid droplet forming unit is not particularly limited and may be appropriately selected depending on the intended purpose so long as the liquid droplet forming unit can form a liquid into a liquid droplet. Examples of the liquid droplet forming unit include an inkjet type, a dispenser type, and a spray drying type. Among these liquid droplet forming units, the dispenser type is preferable because the dispenser type is versatile with a broad range of liquid properties that can be formed into a liquid droplet and can control the size of a liquid droplet by the size of the pore diameter of the head and the pressure for pushing out the liquid filled.

<Surface Coating Step and Surface Coating Unit>

The surface coating step is a step of coating the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 is 50% or higher but 500% or lower.

$$\text{Coating Ratio } CR\ (\%) = \frac{\pi(d50b/2)^2}{4\pi(d50a/2+d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

The surface coating unit is a unit configured to coat the surface of the liquid droplet with composite particles including a hydrophobic solid particle A and a hydrophobic solid particle B over the surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower.

$$\text{Coating Ratio } CR\ (\%) = \frac{\pi(d50b/2)^2}{4\pi(d50a/2+d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

The surface coating step can be suitably performed by the surface coating unit.

The surface coating step in another embodiment is a step of coating the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 is 50% or higher but 500% or lower.

$$\text{Coating Ratio } CR\ (\%) = \frac{\pi(d50b/2)^2}{4\pi(d50a/2+d50b/2)^2} \times \frac{\{X_b(\text{g})/Y_b(\text{g}/\mu\text{m}^3)/Z_b(\mu\text{m}^3)\}}{\{X_a(\text{g})/Y_a(\text{g}/\mu\text{m}^3)/Z_a(\mu\text{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

The surface coating unit in another embodiment is a unit configured to coat the surface of the liquid droplet with composite particles including a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of the number average particle diameter d50a of the hydrophobic solid particle A to the number average particle diameter d50b of the hydrophobic solid particle B is 10 or greater but 100 or less, and wherein a coating ratio CR of the composite particles expressed by Formula 1 below is 50% or higher but 500% or lower.

$$\text{Coating Ratio } CR\ (\%) = \frac{\pi(d50b/2)^2}{4\pi(d50a/2 + d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100 \quad \text{Formula 1}$$

In Formula 1, Xa represents the mass (g) of the hydrophobic solid particles A, Xb represents the mass (g) of the hydrophobic solid particles B, Ya represents the density (g/cubic micrometer) of the hydrophobic solid particles A, Yb represents the density (g/cubic micrometer) of the hydrophobic solid particles B, Za represents the volume (cubic micrometer) of the hydrophobic solid particles A, and Zb represents the volume (cubic micrometer) of the hydrophobic solid particles B.

In the present disclosure, "surface coating" means coating the surface of a liquid droplet. So long as the effect of the present disclosure can be achieved, "coating" may be complete coating of a liquid droplet, or may be partial coating of a liquid droplet.

—Composite Particles—

The composite particles are the same as the composite particles used in the biocatalyst-containing material of the present disclosure.

The method for coating the surface of the liquid droplet is not particularly limited and may be appropriately selected depending on the intended purpose so long as the method can bring the liquid droplet and the composite particles into contact with each other. Examples of the method include a method of spraying the composite particles to the liquid droplet that is flying, and a method of locating a liquid droplet in a container in which the composite particles are densely laid. Of these methods, the method of locating a liquid droplet in a container in which the composite particles are densely laid is preferable in terms of excellent ease of device control.

In the method of locating a liquid droplet in a container in which the composite particles are densely laid, after a liquid droplet is located in the container in which the composite particles are densely laid, it is preferable to add, for example, a step of shaking the container while supplying the composite particles into the container, and a step of inclining the container and rolling the liquid droplet, in order to coat the entire surface of the liquid droplet with the composite particles. These steps may be performed independently, or either step may be performed after the other step is performed.

As the unit configured to supply the composite particles into the container, a commercially available powder supplying apparatus may be used. The mechanism and the type of the powder supplying apparatus may be appropriately selected depending on the conditions of the composite particles.

<Other Steps and Other Units>

The other steps are not particularly limited and may be appropriately selected depending on the intended purpose. Examples of the other steps include a separating step and a collecting step.

The other units are not particularly limited and may be appropriately selected depending on the intended purpose. Examples of the other units include a separating unit and a collecting unit.

The other steps can be suitably performed by the other units. The separating step can be suitably performed by the separating unit. The collecting step can be suitably performed by the collecting unit.

<<Separating Step and Separating Unit>>

The separating step is a step of separating the biocatalyst-containing material from the composite particles left unused for surface coating in the surface coating step.

The separating unit is a unit configured to separate the biocatalyst-containing material from the composite particles left unused for surface coating in the surface coating step.

Examples of the method of separating the biocatalyst-containing material from the composite particles left unused for surface coating in the surface coating step include a method of picking up particles of the biocatalyst-containing material particle by particle, and a method of separating the mixture of the biocatalyst-containing material and the composite particles utilizing the density difference and removing the composite particles. Of these methods, the method utilizing the density difference is preferable in terms of productivity.

Examples of the method of separating the mixture of the biocatalyst-containing material and the composite particles utilizing the density difference and removing the composite particles include a method of passing the mixture through a push-pull dust chamber.

<<Collecting Step and Collecting Unit>>

The collecting step is a step of collecting the biocatalyst-containing material separated.

The collecting unit is a unit configured to collect the biocatalyst-containing material separated.

The method for collecting the biocatalyst-containing material separated is not particularly limited and may be appropriately selected depending on the intended purpose. Examples of the method include a method of letting the biocatalyst-containing material fall from the container to be collected into a collecting container. In order to alleviate the impact of falling, it is preferable to set the collecting container at a distance of within 200 mm from the container, and to incline the collecting container. It is preferable to hydrophobize the internal wall of the collecting container or to form the collecting container using a hydrophobic material.

EXAMPLES

The present disclosure will be described below by way of Examples. The present disclosure should not be construed as being limited to these Examples.

Example A1

—Production of Composite Particles A1—

Polytetrafluoroethylene (PTFE, with a number average particle diameter d50a of 1.0 micrometer, a contact angle CAa of 120 degrees, a mass Xa of 10 g, a density Ya of $2.2\times10^{-12}$ g/cubic micrometer, and a volume Za of 0.52 cubic micrometers, obtained from Sigma-Aldrich Co., LLC., product name: 430935-100G) serving as the hydrophobic solid particles A and hydrophobic silica (with a number average particle diameter d50b of 0.03 micrometers, a contact angle CAb of 170 degrees, a mass Xb of 1.1 g, a density Yb of $1.8\times10^{-12}$ g/cubic micrometer, and a volume Zb of $0.14\times10^{-4}$ cubic micrometers, obtained from Shin-Etsu Chemical Co., Ltd., product name: QSG30) serving as the hydrophobic solid particles B were fed to a V-type container rotary mixer (obtained from Nishimura Machine Works Co., Ltd., device name: NV-5) under an inert gas (nitrogen, 25 degrees C.), and stirred at 10 rpm for 12 hours, to obtain composite particles A1. As the volume of the particles of each kind, the volume of a true sphere having the number average particle diameter, calculated assuming that the particles were a true sphere, was used.

—Production of Liquid-Encapsulating Particles 1—

Next, using a syringe having a 32G syringe needle, liquid droplets were formed at the atmospheric pressure at room temperature (25 degrees C.) at a rate of one droplet per second from a solution obtained by dissolving D-glucose (obtained from Tokyo Chemical Industry Co., Ltd., product name: G0048) in water to have a concentration of 20% by mass. The formed liquid droplets were located in a container (formed of PTFE) in which the composite particles A1 were densely laid, to produce liquid-encapsulating particles A1.

Examples A2 to A21 and Comparative Examples A1 to A17

Composite particles A2 to A38 and liquid-encapsulating particles A2 to A38 were produced in the same manner as in Example A1, except that unlike in Example A1, the compositions were changed to as presented in Tables A1-1 and A1-2 and Table A2.

TABLE A1-1

| | | Composite particles | | | | | | |
|---|---|---|---|---|---|---|---|---|
| | | | Solid particle A | | | | | |
| | | No. | Material | d50a (micrometer) | Mass Xa (g) | Density Ya (g/cubic micrometer) | Volume Za (cubic micrometer) | Contact angle CAa (degree) |
| Ex. A | 1 | 1 | PTFE | 1.0 | 10.0 | 2.20E−12 | 0.52 | 120 |
| | 2 | 2 | PTFE | 1.0 | 10 | 2.20E−12 | 0.52 | 120 |
| | 3 | 3 | PTFE | 1.0 | 10 | 2.20E−12 | 0.52 | 120 |
| | 4 | 4 | PTFE | 1.0 | 10 | 2.20E−12 | 0.52 | 120 |
| | 5 | 5 | PTFE | 1.0 | 10 | 2.20E−12 | 0.52 | 120 |
| | 6 | 6 | PTFE | 1.0 | 10 | 2.20E−12 | 0.52 | 120 |
| | 7 | 7 | PTFE | 0.50 | 10 | 2.20E−12 | 0.07 | 120 |
| | 8 | 8 | PTFE | 1.0 | 10 | 2.20E−12 | 0.52 | 120 |
| | 9 | 9 | Hydrophobic silica | 0.30 | 100 | 1.90E−12 | 1.4E−02 | 170 |
| | 10 | 10 | Stearic acid-treated calcium carbonate | 10 | 10 | 2.80E−12 | 524 | 145 |
| | 11 | 11 | Hydrophobized starch | 20 | 100 | 1.70E−12 | 4,189 | 110 |
| | 12 | 12 | PTFE | 1.0 | 10 | 2.20E−12 | 0.52 | 120 |
| | 13 | 13 | PTFE | 1.0 | 100 | 2.20E−12 | 0.52 | 120 |
| | 14 | 14 | PTFE | 0.50 | 10 | 2.20E−12 | 0.07 | 120 |
| | 15 | 15 | PTFE | 1.0 | 10 | 2.20E−12 | 0.52 | 120 |
| | 16 | 16 | PTFE | 1.0 | 10 | 2.20E−12 | 0.52 | 120 |
| | 17 | 17 | PTFE | 1.0 | 10 | 2.20E−12 | 0.52 | 120 |
| | 18 | 18 | PTFE | 1.0 | 10 | 2.20E−12 | 0.52 | 120 |
| | 19 | 19 | PTFE | 1.0 | 10 | 2.20E−12 | 0.52 | 120 |
| | 20 | 20 | PTFE | 1.0 | 10 | 2.20E−12 | 0.52 | 120 |
| | 21 | 21 | PTFE | 1.0 | 10 | 2.20E−12 | 0.52 | 120 |

TABLE A1-2

| | | Composite particles | | | | | | |
|---|---|---|---|---|---|---|---|---|
| | | | Solid particle B | | | | | |
| | | No. | Material | d50b (micrometer) | Mass Xb (g) | Density Yb (g/cubic micrometer) | Volume Zb (cubic micrometer) | Contact angle CAb (degree) |
| Ex. A | 1 | 1 | Hydrophobic silica | 0.03 | 0.52 | 1.80E−12 | 1.4E−05 | 170 |
| | 2 | 2 | Hydrophobic silica | 0.030 | 0.63 | 1.80E−12 | 1.4E−05 | 170 |
| | 3 | 3 | Hydrophobic silica | 0.030 | 1.06 | 1.80E−12 | 1.4E−05 | 170 |
| | 4 | 4 | Hydrophobic silica | 0.030 | 2.11 | 1.80E−12 | 1.4E−05 | 170 |
| | 5 | 5 | Hydrophobic silica | 0.030 | 5.28 | 1.80E−12 | 1.4E−05 | 170 |
| | 6 | 6 | Hydrophobic silica | 0.010 | 0.34 | 1.80E−12 | 5.2E−07 | 170 |
| | 7 | 7 | Hydrophobic silica | 0.010 | 0.69 | 1.80E−12 | 5.2E−07 | 170 |
| | 8 | 8 | Hydrophobized starch | 0.050 | 1.73 | 1.70E−12 | 6.5E−05 | 110 |
| | 9 | 9 | Fumed silica | 0.015 | 0.46 | 4.00E−14 | 1.8E−06 | 175 |
| | 10 | 10 | Hydrophobic silica | 0.17 | 0.45 | 1.80E−12 | 2.6E−03 | 170 |
| | 11 | 11 | Hydrophobic silica | 118 | 0.64 | 1.80E−12 | 1.4E−05 | 170 |
| | 12 | 12 | Hydrophobic silica | 0.030 | 3.12 | 1.80E−12 | 1.4E−05 | 170 |
| | 13 | 13 | Fumed silica | 0.015 | 0.12 | 4.00E−14 | 1.8E−06 | 175 |
| | 14 | 14 | Hydrophobized starch | 0.050 | 3.75 | 1.70E−12 | 6.5E−05 | 110 |
| | 15 | 15 | Hydrophobic silica | 0.030 | 3.12 | 1.80E−12 | 1.4E−05 | 170 |
| | 16 | 16 | Hydrophobic silica | 0.030 | 3.12 | 1.80E−12 | 1.4E−05 | 170 |
| | 17 | 17 | Hydrophobic silica | 0.030 | 1.06 | 1.80E−12 | 1.4E−05 | 170 |

TABLE A1-2-continued

| | Composite particles | | | | | | |
|---|---|---|---|---|---|---|---|
| | | Solid particle B | | | | | |
| | No. | Material | d50b (micrometer) | Mass Xb (g) | Density Yb (g/cubic micrometer) | Volume Zb (cubic micrometer) | Contact angle CAb (degree) |
| 18 | 18 | Hydrophobic silica | 0.030 | 1.06 | 1.80E−12 | 1.4E−05 | 170 |
| 19 | 19 | Hydrophobic silica | 0.030 | 1.06 | 1.80E−12 | 1.4E−05 | 170 |
| 20 | 20 | Hydrophobic silica | 0.030 | 1.06 | 1.80E−12 | 1.4E−05 | 170 |
| 21 | 21 | Hydrophobic silica | 0.030 | 1.06 | 1.80E−12 | 1.4E−05 | 170 |

TABLE A2-1

| | | Composite particles | | | | | | |
|---|---|---|---|---|---|---|---|---|
| | | | Solid particle A | | | | | |
| | | No. | Material | d50a (micrometer) | Mass Xa (g) | Density Ya (g/cubic micrometer) | Volume Za (cubic micrometer) | Contact angle CAa (degree) |
| Comp. Ex. A | 1 | 22 | Lactose | 30 | 100 | 1.50E−12 | 14,137 | — |
| | 2 | 23 | PTFE | 1.0 | 10 | 2.20E−12 | 0.52 | 120 |
| | 3 | 24 | Stearic acid-treated calcium carbonate | 10 | 100 | 2.80E−12 | 524 | 145 |
| | 4 | 25 | PTFE | 1.0 | 10 | 2.20E−12 | 0.52 | 120 |
| | 5 | 26 | Polystyrene | 20 | 100 | 1.10E−12 | 4,189 | 85 |
| | 6 | 27 | Polystyrene | 20 | 10 | 1.10E−12 | 4,189 | 85 |
| | 7 | 28 | PTFE | 1.0 | 10 | 2.20E−12 | 0.52 | 120 |
| | 8 | 29 | PTFE | 1.0 | 10 | 2.20E−12 | 0.52 | 120 |
| | 9 | 30 | Hydrophobic silica | 0.30 | 10 | 1.90E−12 | 1.4E−02 | 170 |
| | 10 | 31 | — | — | — | — | — | — |
| | 11 | 32 | PTFE | 1.0 | 10 | 2.20E−12 | 0.52 | 120 |
| | 12 | 33 | PTFE | 1.0 | 10 | 2.20E−12 | 0.52 | 120 |
| | 13 | 34 | PTFE | 1.30 | 10.0 | 2.20E−12 | 0.52 | 120 |
| | 14 | 35 | PTFE | 1.00 | 100.0 | 2.20E−12 | 0.52 | 120 |
| | 15 | 36 | PTFE | 1.00 | 10.0 | 2.20E−12 | 0.52 | 120 |
| | 16 | 38 | PTFE | 1.0 | 10 | 2.20E−12 | 0.52 | 120 |
| | 17 | 38 | Polystyrene | 1.5 | 100 | 1.10E−12 | 4,189 | 85 |

TABLE A2-2

| | | Composite particles | | | | | | |
|---|---|---|---|---|---|---|---|---|
| | | | Solid particle B | | | | | |
| | | No. | Material | d50b (micrometer) | Mass Xb (g) | Density Yb (g/cubic micrometer) | Volume Zb (cubic micrometer) | Contact angle CAb (degree) |
| Comp. Ex. A | 1 | 22 | Hydrophobic silica | 0.030 | 0.48 | 1.80E−12 | 1.4E−05 | 170 |
| | 2 | 23 | Lactose | 0.50 | 31.11 | 1.50E−12 | 6.5E−02 | — |
| | 3 | 24 | Hydrophobic silica | 0.010 | 0.26 | 1.80E−12 | 5.2E−07 | 170 |
| | 4 | 25 | Polystyrene | 1.5 | 190.09 | 1.10E−12 | 1.8E+00 | 85 |
| | 5 | 26 | Hydrophobic silica | 0.030 | 0.98 | 1.80E−12 | 1.4E−05 | 170 |
| | 6 | 27 | Polystyrene | 1.5 | 3.47 | 1.10E−12 | 1.8E+00 | 85 |
| | 7 | 28 | PTFE | 0.50 | 45.00 | 2.20E−12 | 6.5E−02 | 120 |
| | 8 | 29 | — | — | — | — | — | — |
| | 9 | 30 | — | — | — | — | — | — |
| | 10 | 31 | Hydrophobic silica | 0.030 | 10.00 | 1.80E−12 | 1.4E−05 | 170 |
| | 11 | 32 | Hydrophobic silica | 0.030 | 0.42 | 1.80E−12 | 1.4E−05 | 170 |
| | 12 | 33 | Hydrophobic silica | 0.030 | 31.68 | 1.80E−12 | 1.4E−05 | 170 |
| | 13 | 34 | Hydrophobic silica | 0.010 | 0.60 | 1.80E−12 | 5.2E−07 | 170 |
| | 14 | 35 | Hydrophobic silica | 0.170 | 0.42 | 1.80E−12 | 1.4E−05 | 170 |
| | 15 | 36 | Hydrophobic silica | 0.030 | 5.72 | 1.80E−12 | 1.4E−05 | 170 |
| | 16 | 37 | Polystyrene | 0.075 | 190.09 | 1.10E−12 | 1.8E+00 | 85 |
| | 17 | 38 | Hydrophobic silica | 0.030 | 31.68 | 1.80E−12 | 1.4E−05 | 170 |

TABLE A3

| | | Composite particles | | | |
|---|---|---|---|---|---|
| | | Particle diameter ratio | Coating ratio CR | Components other than solid particle A and solid particle B | |
| | | d50a/d50b | (%) | Material | Content (% by mass) |
| Ex. A | 1 | 33 | 49.9 | — | — |
| | 2 | 33 | 60.8 | — | — |
| | 3 | 33 | 100 | — | — |
| | 4 | 33 | 200 | — | — |
| | 5 | 33 | 500 | — | — |
| | 6 | 100 | 100 | — | — |
| | 7 | 50 | 100 | — | — |
| | 8 | 20 | 100 | — | — |
| | 9 | 20 | 100 | — | — |
| | 10 | 59 | 100 | — | — |
| | 11 | 118 | 100 | — | — |
| | 12 | 33 | 299.5 | — | — |
| | 13 | 67 | 106.8 | — | — |
| | 14 | 10 | 100.3 | — | — |
| | 15 | 33 | 299.5 | — | — |
| | 16 | 33 | 299.5 | — | — |
| | 17 | 33 | 100 | Zinc stearate | 5.0 |
| | 18 | 33 | 100 | — | — |
| | 19 | 33 | 100 | — | — |
| | 20 | 33 | 100 | — | — |

TABLE A3-continued

| | | Composite particles | | | |
|---|---|---|---|---|---|
| | | Particle diameter ratio | Coating ratio CR | Components other than solid particle A and solid particle B | |
| | | d50a/d50b | (%) | Material | Content (% by mass) |
| | 21 | 33 | 100 | — | — |
| Comp. Ex. A | 1 | 1,000 | 100 | — | — |
| | 2 | 2 | 100 | — | — |
| | 3 | 1,000 | 100 | — | — |
| | 4 | 0.67 | 100 | — | — |
| | 5 | 666.7 | 100 | — | — |
| | 6 | 13.3 | 100 | — | — |
| | 7 | 2 | 100 | — | — |
| | 8 | — | — | — | — |
| | 9 | — | — | — | — |
| | 10 | — | — | — | — |
| | 11 | 33 | 40 | — | — |
| | 12 | 33 | 3000 | — | — |
| | 13 | 130 | 106.8 | — | — |
| | 14 | 6 | 100.3 | — | — |
| | 15 | 33 | 549.1 | — | — |
| | 16 | 13 | 100 | — | — |
| | 17 | 33 | 100 | — | — |

TABLE A4

| | | Liquid | | | | | | | Number average particle diameter d50c (mm) of liquid-encapsulating particle |
|---|---|---|---|---|---|---|---|---|---|
| | | Water content (%) | Second component: Material | Second component: Content (% by mass) | Third component: Material | Third component: Content (% by mass) | Contact angle CALa (degree) | Contact angle CALb (degree) | |
| Ex A | 1 | 80.0 | D-glucose | 20 | — | — | 120 | 170 | 1.3 |
| | 2 | 80.0 | D-glucose | 20 | — | — | 120 | 170 | 1.3 |
| | 3 | 80.0 | D-glucose | 20 | — | — | 120 | 170 | 1.2 |
| | 4 | 80.0 | D-glucose | 20 | — | — | 120 | 170 | 1.3 |
| | 5 | 80.0 | D-glucose | 20 | — | — | 120 | 170 | 1.1 |
| | 6 | 80.0 | D-glucose | 20 | — | — | 120 | 170 | 1.3 |
| | 7 | 80.0 | D-glucose | 20 | — | — | 120 | 170 | 1.4 |
| | 8 | 80.0 | D-glucose | 20 | — | — | 120 | 170 | 1.3 |
| | 9 | 80.0 | D-glucose | 20 | — | — | 170 | 175 | 1.2 |
| | 10 | 80.0 | D-glucose | 20 | — | — | 145 | 170 | 1.5 |
| | 11 | 80.0 | D-glucose | 20 | — | — | — | 170 | 1.8 |
| | 12 | 80.0 | D-glucose | 20 | — | — | 120 | 170 | 1.1 |
| | 13 | 80.0 | D-glucose | 20 | — | — | 120 | 170 | 1.1 |
| | 14 | 80.0 | D-glucose | 20 | — | — | 120 | 170 | 1.1 |
| | 15 | 80.0 | D-glucose | 20 | — | — | 120 | 170 | 0.015 |
| | 16 | 80.0 | D-glucose | 20 | — | — | 120 | 170 | 2.5 |
| | 17 | 80.0 | D-glucose | 20 | — | — | 120 | 170 | 1.5 |
| | 18 | 15.0 | D-glucose | 40 | Official honey | 45 | 100 | 160 | 1.4 |
| | 19 | 60.0 | D-glucose | 20 | Official honey | 20 | 105 | 165 | 1.5 |
| | 20 | 79.5 | D-glucose | 20 | Ascorbic acid | 0.5 | 110 | 165 | 1.6 |
| | 21 | 100 | — | — | — | — | — | — | 1.2 |
| Comp. Ex. A | 1 | 80.0 | D-glucose | 20 | — | — | 120 | 170 | — |
| | 2 | 80.0 | D-glucose | 20 | — | — | 120 | 170 | 1.9 |
| | 3 | 80.0 | D-glucose | 20 | — | — | 140 | 170 | 1.3 |
| | 4 | 80.0 | D-glucose | 20 | — | — | 140 | 170 | 1.5 |
| | 5 | 80.0 | D-glucose | 20 | — | — | 140 | 170 | 1.4 |
| | 6 | 80.0 | D-glucose | 20 | — | — | 80 | 80 | — |
| | 7 | 80.0 | D-glucose | 20 | — | — | 140 | 170 | 1.3 |
| | 8 | 80.0 | D-glucose | 20 | — | — | 120 | 170 | 1.4 |
| | 9 | 80.0 | D-glucose | 20 | — | — | 120 | 170 | 1.7 |
| | 10 | 100 | — | — | — | — | — | — | 1.4 |
| | 11 | 80.0 | D-glucose | 20 | — | — | 120 | 170 | 1.5 |
| | 12 | 80.0 | D-glucose | 20 | — | — | 120 | 170 | 1.1 |
| | 13 | 80.0 | D-glucose | 20 | — | — | 120 | 170 | 1.4 |
| | 14 | 80.0 | D-glucose | 20 | — | — | 120 | 170 | 1.4 |

TABLE A4-continued

| | Liquid | | | | | | | Number average |
|---|---|---|---|---|---|---|---|---|
| | | Second component | | Third component | | Contact angle | | particle diameter d50c (mm) of liquid-encapsulating particle |
| | Water content (%) | Material | Content (% by mass) | Material | Content (% by mass) | CALa (degree) | CALb (degree) | |
| 15 | 80.0 | D-glucose | 20 | — | — | 120 | 170 | 1.4 |
| 16 | 80.0 | D-glucose | 20 | — | — | 120 | 80 | 1.1 |
| 17 | 80.0 | D-glucose | 20 | — | — | 80 | 170 | 1.1 |

The details of the materials used in Examples and Comparative Examples are as follows.

—Hydrophobic Solid Particles A—

Polytetrafluoroethylene (PTFE, with a number average particle diameter d50a of 1.3 micrometers, 1.0 micrometer, and 0.50 micrometers, a contact angle CAa of 120 degrees, and a density Ya of $2.2\times10^{-12}$ g/cubic micrometer, obtained from Sigma-Aldrich Co., LLC., product name: 430935-100G)

Hydrophobic silica (with a number average particle diameter d50a of 0.30 micrometers, a contact angle CAa of 170 degrees, and a density Ya of $1.9\times10^{-12}$ g/cubic micrometer, obtained from Nippon Shokubai Co. Ltd., product name: E30) immersed in hexamethylene disilazane (obtained from Tokyo Chemical Industry Co., Ltd.), filtrated, and heated at 120 degrees C.

Stearic acid-treated calcium carbonate (with a number average particle diameter d50a of 10 micrometers, a contact angle CAa of 145 degrees, and a density Ya of $2.8\times10^{-12}$ g/cubic micrometer), obtained by mixing calcium carbonate (obtained from Tokyo Chemical Industry Co., Ltd.) (100 g) with stearic acid (obtained from Tokyo Chemical Industry Co., Ltd.) (10 g) and methanol (obtained from Tokyo Chemical Industry Co., Ltd.) (500 ml) and subsequently evaporating methanol at reduced pressure and heating the resultant at 50 degrees C. for drying.

Hydrophobized starch (with a number average particle diameter d50a of 20 micrometers, a contact angle CAa of 110 degrees, and a density Ya of $1.7\times10^{-12}$ g/cubic micrometer, obtained from Nippon Starch Chemical Co., Ltd., product name: OCTIE)

—Other Solid Particles A—

Lactose (with a number average particle diameter d50a of 30 micrometers, a contact angle CAa of 0 degrees when dissolved, and a density Ya of $1.5\times10^{-12}$ g/cubic micrometer, obtained from Yoneyama Yakuhin Kogyo Co., Ltd., product name: LACTOSE)

Polystyrene (with a number average particle diameter d50a of 20 micrometers, a contact angle CAa of 85 degrees, and a density Ya of $1.1\times10^{-12}$ g/cubic micrometer, obtained from Sigma-Aldrich Co., LLC., product name: POLYSTYRENE MICROPARTICLES 84135-5ML-F)

—Hydrophobic Solid Particles B—

Hydrophobic silica (with a number average particle diameter d50b of 0.17 micrometers, 0.030 micrometers, and 0.010 micrometers, a contact angle CAb of 170 degrees, and a density Yb of $1.8\times10^{-12}$ g/cubic micrometer, obtained from Shin-Etsu Chemical Co., Ltd., product name: QSG170, QSG30, and QSG10)

Hydrophobized starch (with a number average particle diameter d50b of 0.050 micrometers, a contact angle CAb of 110 degrees, and a density Yb of $1.7\times10^{-12}$ g/cubic micrometer, obtained from Nippon Starch Chemical Co., Ltd., product name: OCTIE)

Polytetrafluoroethylene (PTFE, with a number average particle diameter d50b of 1.0 micrometer and 0.50 micrometers, a contact angle CAb of 120 degrees, and a density Yb of $2.2\times10^{-12}$ g/cubic micrometer, obtained from Sigma-Aldrich Co., LLC., product name: 430935-100G)

Fumed silica (with a number average particle diameter d50b of 0.015 micrometers, a contact angle CAb of 175 degrees, and a density Yb of $4.0\times10^{-14}$ g/cubic micrometer, obtained from Wacker Chemicals Co., Ltd., product name: HDK-H18)

Polystyrene (with a number average particle diameter d50b of 1.5 micrometers, a contact angle CAb of 85 degrees, and a density Yb of $1.1\times10^{-12}$ g/cubic micrometer, obtained from Sigma-Aldrich Co., LLC., product name: POLYSTYRENE MICROPARTICLES 79166-5ML-F)

Polystyrene (with a number average particle diameter d50b of 0.075 micrometers, a contact angle CAb of 85 degrees, and a density Yb of $1.1\times10^{-12}$ g/cubic micrometer, obtained from Creative Diagnostics Inc., Product name: DIAGPOLY™ PLAIN POLYSTYRENE PARTICLES, from 0.05 micrometers through 0.1 micrometers)

—Other Solid Particles B—

Lactose (with a number average particle diameter d50b of 0.50 micrometers, a contact angle CAb of 0 degrees when dissolved, and a density Yb of $1.5\times10^{-12}$ g/cubic micrometer, obtained from Yoneyama Yakuhin Kogyo Co., Ltd.)

—Liquid—

D-glucose (obtained from Tokyo Chemical Industry Co., Ltd.)

Official honey (obtained from Nakakita Co., Ltd.)

Ascorbic acid (obtained from Tokyo Chemical Industry Co., Ltd.)

—Other Components—

Zinc stearate (with a number average particle diameter d50b of 15 micrometers, a contact angle CAb of 85 degrees, and a density of $1.1\times10^{-12}$ g/cubic micrometer, obtained from Yoneyama Yakuhin Kogyo Co., Ltd.)

Next, “coalescing suppressibility” and “durability” of the liquid-encapsulating particles A1 to A38 obtained in Examples A1 to A21 and Comparative Examples A1 to A17 were measured and evaluated in the manners described below. The results are presented in Table A5.

<Evaluation of Coalescing Suppressibility>

—Evaluation 1—

A glass petri dish having a diameter of 30 mm was washed with a neutral detergent, then immersed in a saturated sodium hydroxide aqueous solution for 8 hours or longer, and then rinsed and washed with pure water. After dried sufficiently, the glass petri dish was left to stand still for 12 hours in a tightly closed container filled with hexamethylene disilazane vapor. The resultant glass petri dish was used as a glass petri dish for evaluation 1.

The composite particles were added in the glass petri dish for evaluation 1 in a manner that the composite particles would have a thickness of about 2 mm from the bottom surface. While the resultant glass petri dish for evaluation 1 was gyratorily shaken at 20 rpm with a gyratory shaker (obtained from Corning Inc.), a liquid were dropped in 10 microliters with a microsyringe. One minute later, the liquid was dropped in another 10 microliters. When two liquid-encapsulating particles coalesced into one particle through another one minute of gyratory shaking, the rating of the evaluation was E. When no two liquid-encapsulating particles coalesced, evaluation 2 was performed.

—Evaluation 2—

The composite particles were added in a PTFE-made container having a diameter of 72 mm and a height of 89 mmH in a manner that the composite particles would have a thickness of about 50 mm from the bottom surface, and the resultant container was gyratorily shaken at 200 rpm with a gyratory shaker (obtained from Corning Inc.). With a dispenser (obtained from Musashi Engineering, Inc.), liquid droplets (of the liquid having the composition described in Table A4) having a diameter of 1 mm were discharged into the container at a rate of one droplet per second.

After 1,000 droplets were discharged, the inside of the container was visually observed. When any liquid-encapsulating particles had coalesced and exploded to form a film of the composite particles over the water surface, the rating of the evaluation was D. When no film of the composite particles had formed over the water surface, more liquid droplets were discharged.

After a total of 2,000 droplets were discharged, the inside of the container was visually observed. When any liquid-encapsulating particles had coalesced and exploded to form a film of the composite particles over the water surface, the rating of the evaluation was C. When no film of the composite particles had formed over the water surface, more liquid droplets were discharged.

After a total of 3,000 droplets were discharged, the inside of the container was visually observed. When any liquid-encapsulating particles had coalesced and exploded to form a film of the composite particles over the water surface, the rating of the evaluation was B. When no film of the composite particles had formed over the water surface, the rating of the evaluation was A.

Scores were calculated according to the evaluation criteria described below.

[Evaluation Criteria]

A: 10 points

B: 8 points

C: 6 points

D: 4 points

E: 0 points

<Evaluation of Durability>

A 1 mL vial was filled with the produced liquid-encapsulating particles (500 mg) and capped. The resultant was used as a measurement sample. The measurement sample was let to freely fall onto a wood block from a height of 200 mm, and the inside of the vial was visually observed. This operation was repeated until all of the liquid-encapsulating particles exploded and no longer had the particle shape. The number of times of this operation when all of the liquid-encapsulating particles exploded was obtained as a measurement, and scores were calculated according to the evaluation criteria described below.

[Evaluation Criteria]

Six times or more: 10 points

Five times: 8 points

Four times: 6 points

Three times: 4 points

Two times: 2 points

One time or less: 0 points

<Total Evaluation>

The total of the scores of "coalescing suppressibility" and "durability" was evaluated according to the evaluation criteria described below. A product that scored 0 points in any of the evaluations was given the worst rating "Failure". Products with the ratings "E" and "Failure" are not industrially applicable.

[Evaluation Criteria]

A: Higher than 18 points but 20 points or lower

B: Higher than 16 points but 18 points or lower

C: Higher than 12 points but 16 points or lower

D: Higher than 8 points but 12 points or lower

E: 8 points or lower

TABLE A5

| | | Evaluation result | | | | | |
|---|---|---|---|---|---|---|---|
| | | Coalescing suppressibility | | Durability | | Total evaluation | |
| | | Rating | Score | Number of times | Score | Score | Rating |
| Ex. A | 1 | C | 6 | 4 | 6 | 12 | B |
| | 2 | B | 8 | 4 | 6 | 14 | C |
| | 3 | A | 10 | 5 | 8 | 18 | B |
| | 4 | A | 10 | 4 | 6 | 16 | B |
| | 5 | B | 8 | 4 | 6 | 14 | C |
| | 6 | C | 6 | 3 | 4 | 10 | D |
| | 7 | A | 10 | 5 | 8 | 18 | B |
| | 8 | C | 6 | 3 | 4 | 10 | D |
| | 9 | C | 6 | 3 | 4 | 10 | D |
| | 10 | C | 6 | 3 | 4 | 10 | D |
| | 11 | C | 6 | 3 | 4 | 10 | D |
| | 12 | A | 10 | 6 | 10 | 20 | A |
| | 13 | A | 10 | 6 | 10 | 20 | A |
| | 14 | C | 6 | 3 | 4 | 10 | D |
| | 15 | A | 10 | 6 | 10 | 20 | A |
| | 16 | C | 6 | 3 | 4 | 10 | D |
| | 17 | A | 10 | 5 | 8 | 18 | B |
| | 18 | A | 10 | 6 | 10 | 20 | A |
| | 19 | A | 10 | 5 | 8 | 18 | B |
| | 20 | A | 10 | 4 | 6 | 16 | C |
| | 21 | C | 6 | 3 | 4 | 10 | D |
| Comp. Ex. A | 1 | E | 0 | — | 0 | 0 | Failure |
| | 2 | D | 4 | 1 | 0 | 4 | Failure |
| | 3 | D | 4 | 2 | 2 | 6 | E |
| | 4 | C | 6 | 2 | 2 | 8 | E |
| | 5 | C | 6 | 2 | 2 | 8 | E |
| | 6 | E | 0 | — | 0 | 0 | Failure |
| | 7 | C | 6 | 2 | 2 | 8 | E |
| | 8 | D | 4 | 1 | 0 | 4 | Failure |
| | 9 | D | 4 | 1 | 0 | 4 | Failure |
| | 10 | D | 4 | 1 | 0 | 4 | Failure |
| | 11 | D | 4 | 1 | 0 | 4 | Failure |
| | 12 | D | 4 | 1 | 0 | 4 | Failure |
| | 13 | C | 6 | 2 | 2 | 8 | E |
| | 14 | D | 4 | 1 | 0 | 4 | Failure |

TABLE A5-continued

| | Evaluation result | | | | | |
|---|---|---|---|---|---|---|
| | Coalescing suppressibility | | Durability | | Total evaluation | |
| | | | Number | | | |
| | Rating | Score | of times | Score | Score | Rating |
| 15 | C | 6 | 2 | 2 | 8 | E |
| 16 | C | 6 | 2 | 2 | 8 | E |
| 17 | D | 4 | 2 | 2 | 6 | E |

Figure 2A:
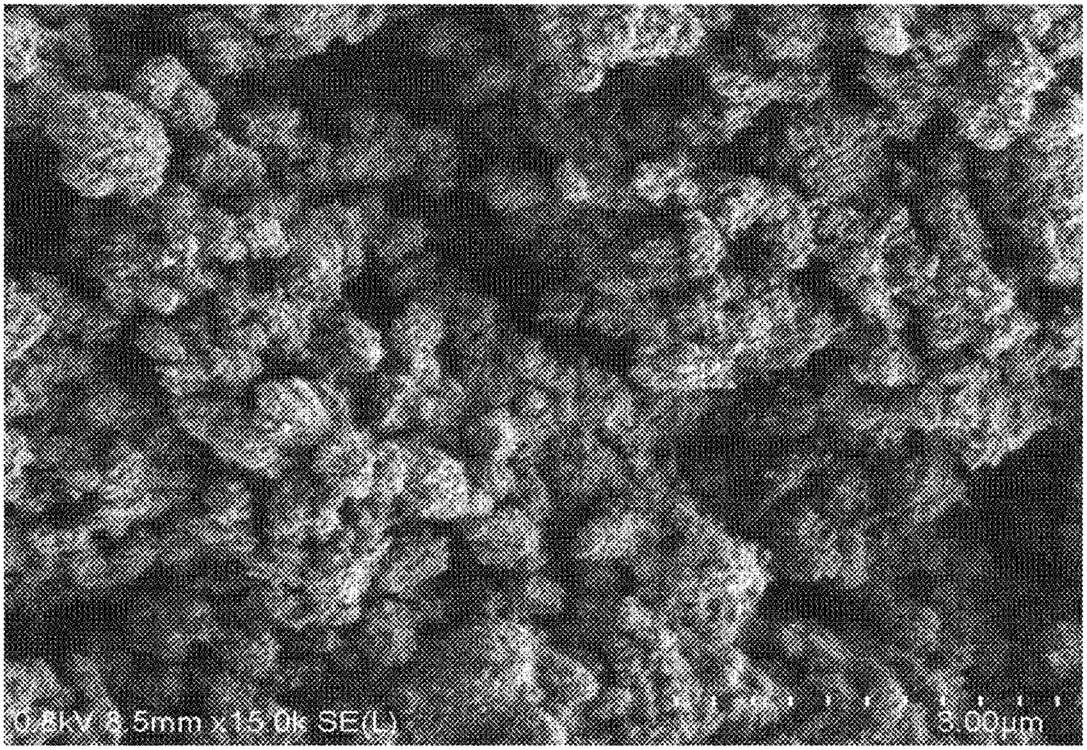
FIG. 2A is a view illustrating an example of an electron microscopic image of composite particles used in Examples A15 and B2.
Figure 2B:
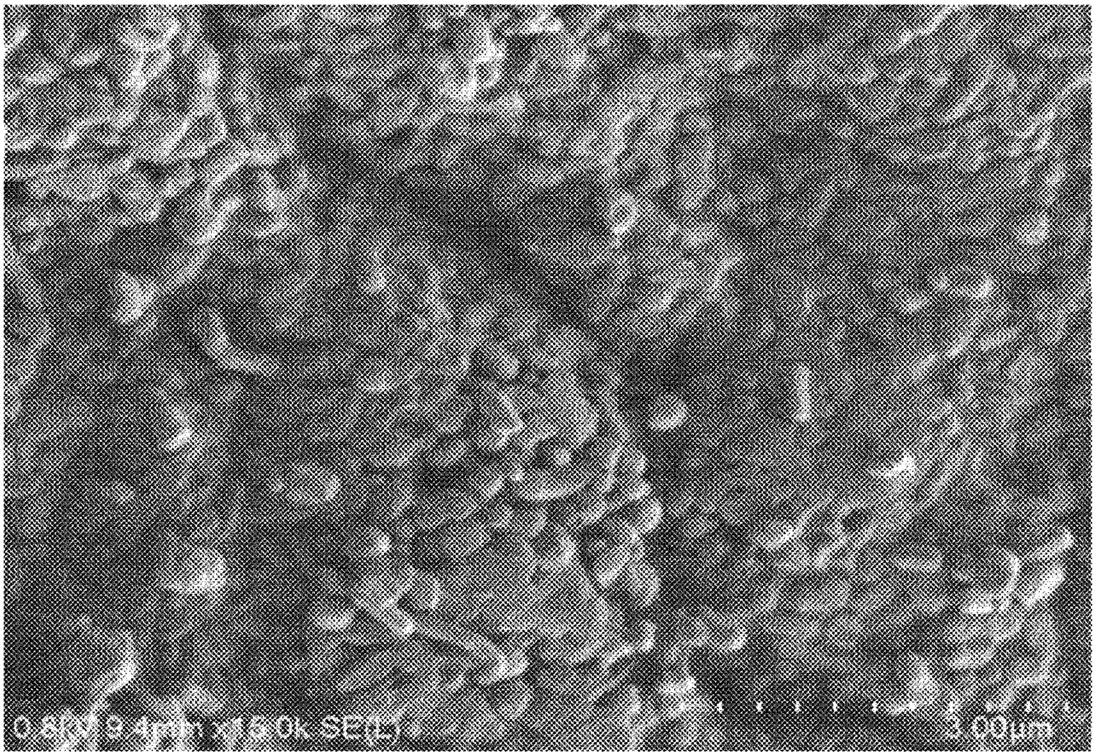
FIG. 2B is a view illustrating an example of an electron microscopic image of hydrophobic solid particles A used in Examples A15 and B2.
Figure 2C:
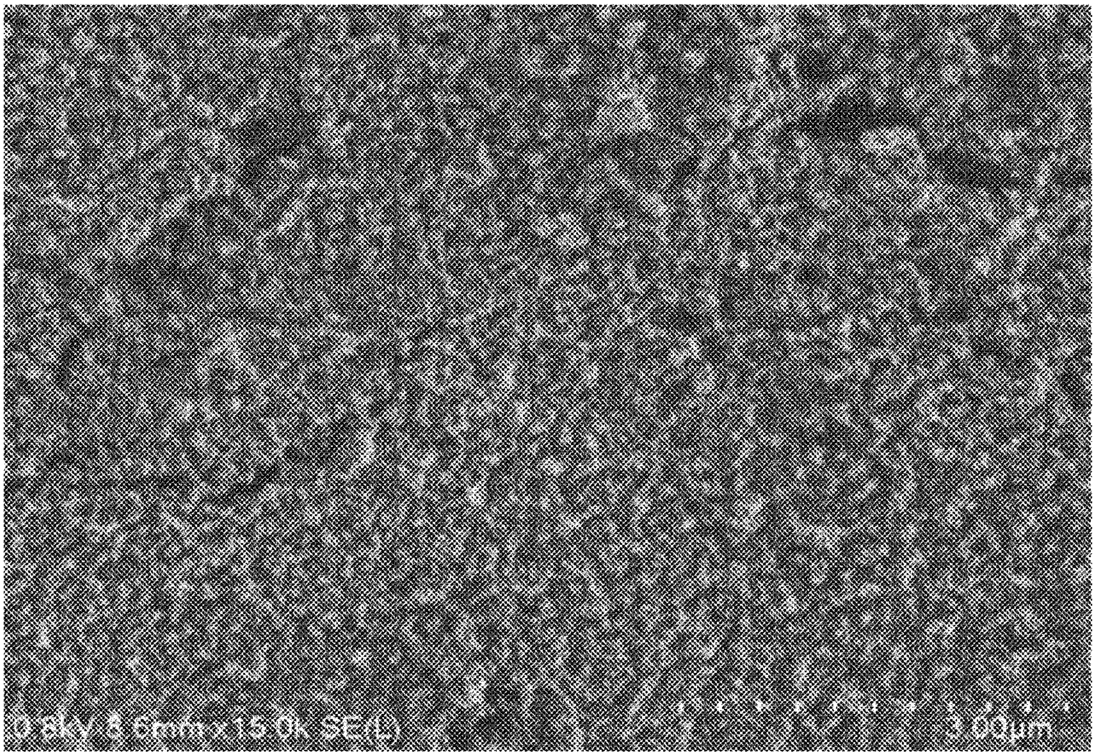
FIG. 2C is a view illustrating an example of an electron microscopic image of hydrophobic solid particles B used in Examples A15 and B2.
Figure 3A:
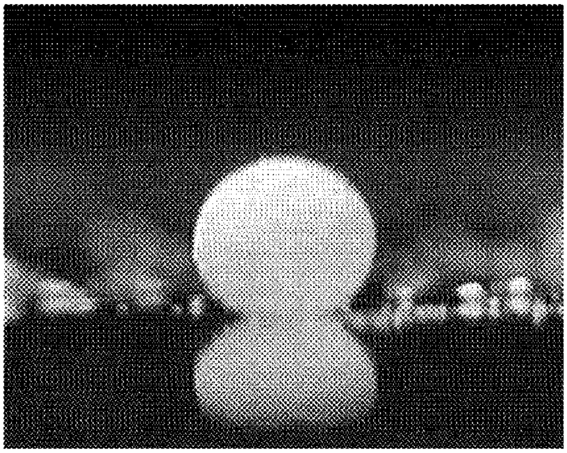
FIG. 3A is a view illustrating an example of an image of liquid-encapsulating particles of Examples A15 and B2.
Figure 3B:
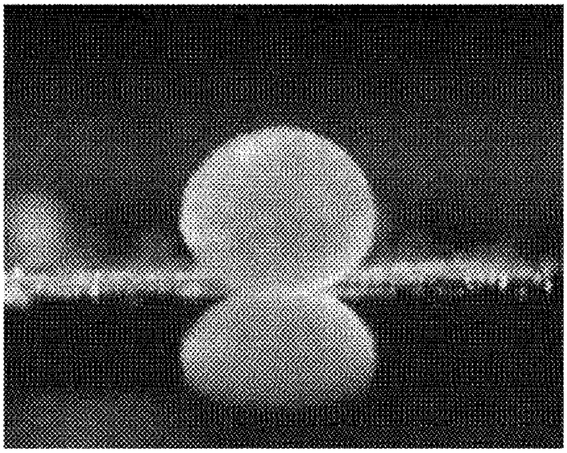
FIG. 3B is a view illustrating an example of an image of liquid-encapsulating particles of Comparative Examples A10 and B6.

FIG. 2A illustrates an electron microscopic image of the composite particles A21 used in Example A21. FIG. 2B illustrates an electron microscopic image of the hydrophobic solid particles A used in Example A21. FIG. 2C illustrates an electron microscopic image of the hydrophobic solid particles B used in Example A21 and Comparative Example A10. FIG. 3A illustrates an image of the liquid-encapsulating particles of Example A21. FIG. 3B illustrates an image of the liquid-encapsulating particles of Comparative Example A10.

It was possible to observe a state that the surface of PTFE, which served as the hydrophobic solid particles A illustrated in FIG. 2B, was coated with hydrophobic silica, which served as the hydrophobic solid particles B illustrated in FIG. 2C, at a coating ratio of 100% as illustrated in FIG. 2A.

The liquid-encapsulating particles obtained using the composite particles illustrated in FIG. 2A had a ratio (longer axis/shorter axis) of 1.34/1.31=1.02 between the length of the longer axis and the length of the shorter axis. As compared, the liquid-encapsulating particles obtained using only hydrophobic silica serving as the hydrophobic solid particles B had a ratio (longer axis/shorter axis) of 1.43/1.31=1.09 between the length of the longer axis and the length of the shorter axis.

Example B1

—Production of Composite Particles B1—

Polytetrafluoroethylene (PTFE, with a number average particle diameter d50a of 1.0 micrometer, a contact angle CAa of 120 degrees, a mass Xa of 10 g, a density Ya of $2.2\times10^{-12}$ g/cubic micrometer, and a volume Za of 0.52 cubic micrometers, obtained from Sigma-Aldrich Co., LLC., product name: 430935-100G) serving as the hydrophobic solid particles A and hydrophobic silica (with a number average particle diameter d50b of 0.030 micrometers, a contact angle CAb of 170 degrees, a mass Xb of 1.1 g, a density Yb of $1.8\times10^{-12}$ g/cubic micrometer, and a volume Zb of $1.4\times10^{-5}$ cubic micrometers, obtained from Shin-Etsu Chemical Co., Ltd., product name: QSG30) serving as the hydrophobic solid particles B were fed to a V-type container rotary mixer (obtained from Nishimura Machine Works Co., Ltd., device name: NV-5) under an inert gas (nitrogen, 25 degrees C.), and stirred at 10 rpm for 12 hours, to obtain composite particles B1. As the volume of the particles of each kind, the volume of a true sphere having the number average particle diameter, calculated assuming that the particles were a true sphere, was used.

—Production of Biocatalyst-Containing Material B1—

Next, a solution obtained by dissolving a yeast fungus (scientific name: *Saccharomyces Cerevisiae*, obtained from Nisshin Seifun Group Inc., product name: DRY YEAST), and D-glucose (obtained from Tokyo Chemical Industry Co., Ltd.) (20% by mass) in water was formed into liquid droplets using a syringe having a 32G syringe needle under the atmosphere at room temperature at a dropping speed of one droplet per second, to locate the formed liquid droplets in a container (formed of PTFE) in which the composite particles B1 were densely laid, to produce a sample B1.

Examples B2 to B24 and Comparative Examples B1 to B6

Samples B2 to B30 were produced in the same manner as in Example B1, except that unlike in Example B1, the composition was changed to as presented in Table B1-1 to Table B6-2. In Comparative Example 3, the solution having the composition presented in Table B1-1 to Table B6-2 was prepared in 100 mL and used for the evaluation described below.

TABLE B1-1

| | | Composite particles | | | | | |
|---|---|---|---|---|---|---|---|
| | | Solid particle A | | | | | |
| | | Material | d50a (micrometer) | Mass Xa (g) | Density Ya (g/cubic micrometer) | Volume Za (cubic micrometer) | Contact angle CAa (degree) |
| Ex. B | 1 | PTFE | 1.0 | 10.0 | 2.20E−12 | 0.524 | 120 |
| | 2 | PTFE | 1.0 | 10.0 | 2.20E−12 | 0.524 | 120 |
| | 3 | PTFE | 1.0 | 10.0 | 2.20E−12 | 0.524 | 120 |
| | 4 | PTFE | 1.0 | 10.0 | 2.20E−12 | 0.524 | 120 |
| | 5 | PTFE | 1.0 | 10.0 | 2.20E−12 | 0.524 | 120 |
| | 6 | PTFE | 0.50 | 10.0 | 2.20E−12 | 6.54E−02 | 120 |
| | 7 | PTFE | 1.0 | 10.0 | 2.20E−12 | 0.524 | 120 |
| Comp. | 1 | PTFE | 1.0 | 10.0 | 2.20E−12 | 0.524 | 120 |
| Ex. B | 2 | PTFE | 1.0 | 10.0 | 2.20E−12 | 0.524 | 120 |

TABLE B1-2

| | | Composite particles | | | | | |
|---|---|---|---|---|---|---|---|
| | | Solid particle B | | | | | |
| | | Material | d50b (micrometer) | Mass Xb, (g) | Density Yb (g/cubic micrometer) | Volume Zb (cubic (micrometer) | Contact angle CAb (degree) |
| Ex. B | 1 | Hydrophobic silica | 0.030 | 0.63 | 1.80E−12 | 1.41E−05 | 170 |
| | 2 | Hydrophobic silica | 0.030 | 1.06 | 1.80E−12 | 1.41E−05 | 170 |
| | 3 | Hydrophobic silica | 0.030 | 5.28 | 1.80E−12 | 1.41E−05 | 170 |
| | 4 | Hydrophobic silica | 0.030 | 1.06 | 1.80E−12 | 1.41E−05 | 170 |
| | 5 | Hydrophobic silica | 0.010 | 0.34 | 1.80E−12 | 5.24E−07 | 170 |
| | 6 | Hydrophobic silica | 0.010 | 0.69 | 1.80E−12 | 5.24E−07 | 170 |
| | 7 | Hydrophobic silica | 0.030 | 1.06 | 1.80E−12 | 1.41E−05 | 170 |
| Comp. Ex. B | 1 | Hydrophobic silica | 0.030 | 1.06 | 1.80E−12 | 1.41E−05 | 170 |
| | 2 | Hydrophobic silica | 0.030 | 1.06 | 1.80E−12 | 1.41E−05 | 170 |

TABLE B2-1

| | | Composite particles | | | | | |
|---|---|---|---|---|---|---|---|
| | | Solid particle A | | | | | |
| | | Material | d50a (micrometer) | Mass Xa (g) | Density Ya (g/cubic micrometer) | Volume Za (cubic micrometer) | Contact angle CAa (degree) |
| Ex B | 8 | PTFE | 1.0 | 10.0 | 2.20E−12 | 0.524 | 120 |
| | 9 | PTFE | 1.0 | 10.0 | 2.20E−12 | 0.524 | 120 |
| | 10 | PTFE | 1.0 | 10.0 | 2.20E−12 | 0.524 | 120 |
| | 11 | PTFE | 1.0 | 10.0 | 2.20E−12 | 0.524 | 120 |
| | 12 | Hydrophobic silica | 0.30 | 100.0 | 1.90E−12 | 1.41E−02 | 170 |
| | 13 | PTFE | 1.30 | 10.0 | 2.20E−12 | 0.524 | 120 |
| | 14 | PTFE | 1.0 | 10.0 | 2.20E−12 | 0.524 | 120 |
| | 15 | PTFE | 0.50 | 10.0 | 2.20E−12 | 6.54E−02 | 120 |
| | 16 | PTFE | 1.0 | 100.0 | 2.20E−12 | 0.524 | 120 |
| | 17 | PTFE | 1.0 | 10.0 | 2.20E−12 | 0.524 | 120 |
| | 18 | PTFE | 1.0 | 10.0 | 2.20E−12 | 0.524 | 120 |
| | 19 | PTFE | 1.0 | 10.0 | 2.20E−12 | 0.524 | 120 |
| | 20 | PFA AGC Inc. ACX-34 | 5.0 | 10.0 | 2.20E−12 | 65.4 | 105 |
| | 21 | PTFE | 1.0 | 10.0 | 2.20E−12 | 0.524 | 120 |
| | 22 | PFA AGC Inc. ACX-34 | 5.0 | 10.0 | 2.20E−12 | 65.4 | 105 |
| | 23 | Hydrophobic silica | 0.30 | 10.0 | 1.80E−12 | 1.41E−02 | 170 |
| | 24 | Hydrophobic silica | 1.0 | 10.0 | 2.10E−12 | 0.524 | 60.0 |
| Comp. Ex. B | 3 | PTFE | 1.0 | 10.0 | 2.20E−12 | 0.524 | 120 |
| | 4 | — | — | — | — | — | — |
| | 5 | PTFE | 1.0 | 10.0 | 2.20E−12 | 0.524 | 120 |
| | 6 | — | — | — | — | — | — |

TABLE B2-2

| | | Composite particles | | | | | |
|---|---|---|---|---|---|---|---|
| | | Solid particle B | | | | | |
| | | Material | d50b (micrometer) | Mass Xb (g) | Density Yb (g/cubic micrometer) | Volume Zb (cubic micrometer) | Contact angle CAb (degree) |
| Ex. B | 8 | Hydrophobic silica | 0.030 | 0.47 | 1.80E−12 | 1.41E−05 | 170 |
| | 9 | Hydrophobic silica | 0.030 | 2.12 | 1.80E−12 | 1.41E−05 | 170 |
| | 10 | Hydrophobic silica | 0.030 | 2.12 | 1.80E−12 | 1.41E−05 | 170 |
| | 11 | Hydrophobic silica | 0.030 | 6.25 | 1.80E−12 | 1.41E−05 | 170 |
| | 12 | Fumed silica | 0.015 | 0.46 | 4.00E−14 | 1.77E−06 | 175 |
| | 13 | Hydrophobic silica | 0.010 | 0.60 | 1.80E−12 | 5.24E−07 | 170 |
| | 14 | Hydrophobic silica | 0.010 | 0.34 | 1.80E−12 | 5.24E−07 | 170 |
| | 15 | Hydrophobic silica | 0.010 | 0.69 | 1.80E−12 | 5.24E−07 | 170 |
| | 16 | Hydrophobic silica | 0.17 | 0.42 | 1.80E−12 | 1.41E−05 | 170 |
| | 17 | Hydrophobic silica | 0.030 | 1.06 | 1.80E−12 | 1.41E−05 | 170 |
| | 18 | Hydrophobic silica | 0.030 | 1.06 | 1.80E−12 | 1.41E−05 | 170 |
| | 19 | Hydrophobic silica | 0.030 | 1.06 | 1.80E−12 | 1.41E−05 | 170 |
| | 20 | Hydrophobic silica | 0.17 | 1.22 | 1.80E−12 | 2.57E−03 | 170 |
| | 21 | Titanium oxide TTO-55(c) | 0.10 | 9.31 | 4.23E−12 | 5.24E−04 | 105 |
| | 22 | Titanium oxide TTO-55(c) | 0.050 | 0.79 | 4.23E−12 | 6.54E−05 | 105 |
| | 23 | Hydrophobic silica | 0.030 | 4.84 | 1.80E−12 | 1.41E−05 | 170 |
| | 24 | Hydrophobic silica | 0.030 | 1.10 | 1.80E−12 | 1.41E−05 | 170 |
| Comp. Ex. B | 3 | Hydrophobic silica | 0.030 | 1.06− | 1.80E−12 | 1.41E−05 | 170 |
| | 4 | — | — | — | — | — | — |
| | 5 | — | — | — | — | — | — |
| | 6 | Hydrophobic silica | 0.030 | 1.06 | 1.80E−12 | 1.41E−05 | 170 |

TABLE B3

| | | Composite particles | |
|---|---|---|---|
| | | Particle diameter ratio (d50a/d50b) | Coating ratio CR (%) |
| Ex. B | 1 | 33 | 60 |
| | 2 | 33 | 100 |
| | 3 | 33 | 500 |
| | 4 | 33 | 100 |
| | 5 | 100 | 100 |
| | 6 | 50 | 100 |
| | 7 | 33 | 100 |
| Comp. Ex. B | 1 | 33 | 100 |
| | 2 | 33 | 100 |

TABLE B4

| | | Composite particles | |
|---|---|---|---|
| | | Particle diameter ratio (d50a/d50b) | Coating ratio CR (%) |
| Ex. B | 8 | 33 | 45 |
| | 9 | 33 | 100 |
| | 10 | 33 | 200 |
| | 11 | 33 | 600 |
| | 12 | 20 | 100 |
| | 13 | 130 | 100 |
| | 14 | 100 | 100 |
| | 15 | 50 | 100 |
| | 16 | 6 | 100 |
| | 17 | 33 | 100 |
| | 18 | 33 | 100 |
| | 19 | 33 | 100 |
| | 20 | 29 | 100 |
| | 21 | 10 | 100 |
| | 22 | 100 | 100 |
| | 23 | 10 | 100 |
| | 24 | 33 | 100 |

TABLE B4-continued

| | | Composite particles | |
|---|---|---|---|
| | | Particle diameter ratio (d50a/d50b) | Coating ratio CR (%) |
| Comp. Ex. B | 3 | 33 | 100 |
| | 4 | — | — |
| | 5 | — | — |
| | 6 | — | — |

TABLE B5

| | | Solution containing biocatalyst | | | | | | | | | Biocatalyst-containing material |
|---|---|---|---|---|---|---|---|---|---|---|---|
| | | Biocatalyst | | Water | Matrix | | Other components | | Content | Contact | |
| | | Kind | Content (% by mass) | Content (% by mass) | Material | Content (% by mass) | Material | Contact (% by mass) | angle CALa (degree) | angle CALb (degree) | Number average particle diameter d50c (micrometer) |
| Ex. B | 1 | Yeast fungus | 0.1 | 79.4 | D glucose | 20 | Glycerin | 0.5 | 150 | 160 | 600 |
| | 2 | Yeast fungus | 0.5 | 79.0 | D glucose | 20 | Glycerin | 0.5 | 140 | 150 | 500 |
| | 3 | Yeast fungus | 1.0 | 78.5 | D glucose | 20 | Glycerin | 0.5 | 120 | 130 | 900 |
| | 4 | Yeast fungus | 0.5 | 79.0 | D glucose | 20 | Glycerin | 0.5 | 140 | 150 | 800 |
| | 5 | Yeast fungus | 0.5 | 79.0 | Official honey | 20 | Glycerin | 0.5 | 110 | 120 | 800 |
| | 6 | Yeast fungus | 0.5 | 19.5 | Official honey | 40 | Glycerin | 40.0 | 105 | 115 | 800 |
| | 7 | Yeast fungus | 0.5 | 79.0 | D glucose | 20 | — | — | 140 | 150 | 500 |
| Comp. Ex. B | 1 | Yeast fungus | 0.5 | 79.0 | D glucose | 20 | Glycerin | 0.5 | 110 | 160 | 5 |
| | 2 | Yeast fungus | 0.5 | 79.0 | D glucose | 20 | Glycerin | 0.5 | 110 | 160 | 1,600 |

TABLE B6-1

| | | Solution containing biocatalyst | | | | | | | | | Biocatalyst-containing material |
|---|---|---|---|---|---|---|---|---|---|---|---|
| | | Biocatalyst | | Water | Matrix | | Other components | | Content | Contact | |
| | | Kind | Content (% by mass) | Content (% by mass) | Material | Content (% by mass) | Material | Contact (% by mass) | angle CALa (degree) | angle CALb (degree) | Number average particle diameter d50c (micrometer) |
| Ex. B | 8 | Yeast fungus | 0.5 | 79.0 | D glucose | 20 | Glycerin | 0.5 | 140 | 150 | 500 |
| | 9 | Yeast fungus | 0.5 | 79.0 | D glucose | 20 | Glycerin | 0.5 | 140 | 150 | 200 |
| | 10 | Yeast fungus | 0.5 | 79.0 | D glucose | 20 | Glycerin | 0.5 | 140 | 150 | 200 |
| | 11 | Yeast fungus | 0.5 | 79.0 | D glucose | 20 | Glycerin | 0.5 | 140 | 150 | 200 |
| | 12 | Yeast fungus | 0.5 | 79.0 | D glucose | 20 | Glycerin | 0.5 | 140 | 150 | 200 |
| | 13 | Yeast fungus | 0.5 | 79.0 | D glucose | 20 | Glycerin | 0.5 | 140 | 150 | 200 |
| | 14 | Yeast fungus | 0.5 | 79.0 | D glucose | 20 | Glycerin | 0.5 | 140 | 150 | 200 |
| | 15 | Yeast fungus | 0.5 | 79.0 | D glucose | 20 | Glycerin | 0.5 | 140 | 150 | 200 |
| | 16 | Yeast fungus | 0.5 | 79.0 | D glucose | 20 | Glycerin | 0.5 | 140 | 150 | 200 |
| | 17 | Yeast fungus | 0.5 | 79.0 | D glucose | 20 | Glycerin | 0.5 | 140 | 150 | 10 |
| | 18 | Yeast fungus | 0.5 | 79.0 | D glucose | 20 | Glycerin | 0.5 | 140 | 150 | 100 |
| | 19 | Yeast fungus | 0.5 | 79.0 | D glucose | 20 | Glycerin | 0.5 | 140 | 150 | 1,000 |
| | 20 | Yeast fungus | 0.5 | 79.0 | D glucose | 20 | Glycerin | 0.5 | 100 | 160 | 600 |

TABLE B6-1-continued

| | Solution containing biocatalyst | | | | | | | | | Biocatalyst-containing material |
|---|---|---|---|---|---|---|---|---|---|---|
| | Biocatalyst | | Water | Matrix | | Other components | | Content | Contact | |
| | Kind | Content (% by mass) | Content (% by mass) | Material | Content (% by mass) | Material | Contact (% by mass) | angle CALa (degree) | angle CALb (degree) | Number average particle diameter d50c (micrometer) |
| 21 | Yeast fungus | 0.5 | 79.0 | D glucose | 20 | Glycerin | 0.5 | 110 | 100 | 500 |
| 22 | Yeast fungus | 0.5 | 79.0 | D glucose | 20 | Glycerin | 0.5 | 95 | 100 | 500 |
| 23 | Yeast fungus | 0.1 | 79.0 | D glucose | 20 | Glycerin | 0.5 | 175 | 175 | 600 |
| 24 | Yeast fungus | 0.5 | 79.0 | D glucose | 20 | Glycerin | 0.5 | 90 | 160 | 500 |

TABLE B6-2

| | | Solution containing biocatalyst | | | | | | | | | Biocatalyst-containing material |
|---|---|---|---|---|---|---|---|---|---|---|---|
| | | Biocatalyst | | Water | Matrix | | Other components | | Content | Contact | |
| | | Kind | Content (% by mass) | Content (% by mass) | Material | Content (% by mass) | Material | Contact (% by mass) | angle CALa (degree) | angle CALb (degree) | Number average particle diameter d50c (micrometer) |
| Comp. Ex. B | 3 | Yeast fungus | 0.5 | 79.0 | D glucose | 20 | Glycerin | 0.5 | 110 | 160 | 1,100 |
| | 4 | Yeast fungus | 0.5 | 79.0 | D glucose | 20 | Glycerin | 0.5 | — | — | — |
| | 5 | Yeast fungus | 0.5 | 79.0 | D glucose | 20 | Glycerin | 0.5 | 110 | — | 500 |
| | 6 | Yeast fungus | 0.5 | 79.0 | D glucose | 20 | Glycerin | 0.5 | — | 160 | 500 |

The details of the materials used in Examples and Comparative Examples are as follows.

—Hydrophobic Solid Particles A—

Polytetrafluoroethylene (PTFE, with a number average particle diameter d50a of 1.0 micrometer and 0.50 micrometers, a contact angle CAa of 120 degrees, and a density Ya of $2.2\times10^{-12}$ g/cubic micrometer, obtained from Sigma-Aldrich Co., LLC., product name: 430935-100G)

Hydrophobic silica (with a number average particle diameter d50a of 0.30 micrometers, a contact angle CAa of 170 degrees, and a density Ya of $1.9\times10^{-12}$ g/cubic micrometer, obtained from Nippon Shokubai Co. Ltd., product name: E30) immersed in hexamethylene disilazane (obtained from Tokyo Chemical Industry Co., Ltd.), filtrated, and heated at 120 degrees C.

Hydrophilic silica (with a number average particle diameter d50a of 1.0 micrometer, a contact angle CAa of 60 degrees, and a density Ya of $2.2\times10^{-12}$ g/cubic micrometer, obtained from Corefront Corporation, product name: MICROMOD)

Perfluoroalkoxyalkane (PFA, with a number average particle diameter d50a of 5.0 micrometers, a contact angle CAa of 105 degrees, and a density Ya of $2.2\times10^{-12}$ g/cubic micrometer, obtained from AGC Inc., product name: ACX-34

—Hydrophobic Solid Particles B—

Hydrophobic silica (with a number average particle diameter d50b of 0.17 micrometers, 0.030 micrometers, and 0.010 micrometers, a contact angle CAb of 170 degrees, and a density Yb of $1.8\times10^{-12}$ g/cubic micrometer, obtained from Shin-Etsu Chemical Co., Ltd., product name: QSG170, QSG30, and QSG10)

Titanium oxide (with a number average particle diameter d50a of 0.10 micrometers and 0.050 micrometers, a contact angle CAa of 105 degrees, and a density Yb of $2.2\times10^{-12}$ g/cubic micrometers, obtained from Ishihara Sangyo Kaisha, Ltd., product name: TTO-55(C))

—Biocatalyst—

Yeast fungus (scientific name: *Saccharomyces Cerevisiae*, obtained from Nisshin Seifun Group Inc., product name: DRY YEAST)

—Matrix—

D-glucose (obtained from Tokyo Chemical Industry Co., Ltd.)

Official honey (obtained from Nakakita Co., Ltd.)

—Other Components—

Glycerin (Obtained from FUJIFILM Wako Pure Chemical Corporation)

Next, “valuable producing efficiency ([evaluation of valuable production] and [evaluation of matrix consumption])” and “durability” of the samples B1 to B7, and B25 and B26 obtained in Examples B1 to B7 and Comparative Examples B1 and B2 were measured and evaluated in the manners described below. The results are presented in Tables 7 and 8. For the samples B8 to B24 and B27 to B30 obtained in Examples B8 to B24 and Comparative Examples B3 to B6, the results of only [evaluation of matrix consumption] are presented in terms of “valuable producing efficiency”

<Valuable Producing Efficiency>

Valuable producing efficiency of the biocatalyst (yeast fungus) was evaluated by conducting “evaluation of valuable production” and “evaluation of matrix consumption”.

<<Evaluation of Valuable Production>>

The produced sample (10 g) was filled in a 200 mL airtight container (product name: GL45 SERIES, obtained from Sibata Scientific Technology Ltd.), and left to stand still at 35 degrees C. in a nitrogen atmosphere for 12 hours. After the leaving to stand still, the container was immersed in a hot-water bath at 70 degrees C. and further left to stand still for 2 hours. Subsequently, a gas (100 mL) was collected from the container and the content ratio of ethanol in the gas was measured. For obtaining the content ratio of ethanol, a Kitagawa gas sampler (AP-20) and an ethanol detection tube (ETHANOL 12) obtained from Gastec Corporation were used. The measured value obtained was used as a production rate A (%).

As a control test, a liquid containing a biocatalyst in the same amount as used for producing the above-described sample (10 g) was filled in the same container, and subsequently left to stand still under the same conditions. A gas was collected in the same manner to measure the content ratio of ethanol. The measured value obtained was used as a production rate B (%).

The difference between the production rate A and the production rate B was defined by the formula below, and evaluated according to the evaluation criteria.

$$\text{Evaluation } C = \text{production rate } A - \text{production rate } B$$

[Evaluation Criteria]

10 points: C was 0.05 or greater.

8 points: C was 0.01 or greater but less than 0.01.

5 points: C was greater than 0 but less than 0.01.

0 points: C was 0 or less.

<<Evaluation of Matrix Consumption>>

The produced sample (10 g) was filled in a 100 mL airtight container (product name: GL45 SERIES, obtained from Sibata Scientific Technology Ltd.), and left to stand still at 35 degrees C. in a nitrogen atmosphere for 12 hours. Subsequently, the liquid component was extracted from the gas phase and the sample in the container, the concentration of the liquid component was measured using a refractometer, and subsequently the amount of the matrix component in the container was measured. The liquid component was extracted by exposing the sample to ethanol vapor and separating the sample into the composite particles and liquid droplets (liquid) by filtration through a 200 micrometer filter.

A matrix consumption ratio A between before and after the reaction was calculated according to the formula below including an amount of supply of the matrix.

$$\text{Matrix consumption ratio } A = \{(\text{amount of matrix before reaction} + \text{total amount of supply of matrix} - \text{total amount of matrix after reaction}) / (\text{amount of matrix before reaction} + \text{total amount of supply of matrix})\} \times 100$$

As a control test, the reaction was performed in the same manner as described above, except that a liquid containing a biocatalyst in the same amount as used for producing the above-described sample (10 g) was filled in the same container and allowed to undergo a substance producing reaction with flow supply of the matrix under the same condition, at the same temperature, atmosphere, and time conditions, and a matrix consumption ratio B between before and after the reaction was calculated according to the formula below including an amount of supply of the matrix.

$$\text{Matrix consumption ratio } B = \{(\text{amount of matrix before reaction} + \text{total amount of supply of matrix} - \text{total amount of matrix after reaction}) / (\text{amount of matrix before reaction} + \text{total amount of supply of matrix})\} \times 100$$

The difference between the matrix consumption ratio A and the matrix consumption ratio B was defined by the formula below, and evaluated according to the evaluation criteria.

$$\text{Evaluation } C = \text{matrix consumption ratio } A - \text{matrix consumption ratio } B$$

[Evaluation Criteria]

10 points: C was 20 or greater.

8 points: C was 10 or greater but less than 20.

5 points: C was greater than 0 but less than 10.

0 points: C was 0 or less.

<Durability Evaluation>

A 1 mL vial was filled with the produced sample (500 mg) and capped to be used as a measurement sample. The measurement sample was let to freely fall onto a wood block from a height of 200 mm, and the inside of the measurement sample was observed. This operation was repeated until all particles of the sample exploded and no longer had the particle shape. The number of times of this operation when all particles of the sample exploded was obtained as a measurement, and the score was calculated according to the evaluation criterial described below.

[Evaluation Criteria]

6 times or more: 10 points 5 times: 8 points 4 times: 6 points 3 times: 4 points 2 times: 2 points 1 time or less: 0 points <Total Evaluation>

The total of the scores of "valuable producing efficiency" and "durability" was evaluated according to the evaluation criteria described below. Any sample that scored 0 points in any of the evaluations was given the worst rating "Failure". Samples with the ratings "D", "E", and "Failure" are not industrially applicable.

Evaluation Criteria: Examples B1 to B7 and Comparative Examples B1 and B2

A: 27 points or higher but 30 points or lower

B: 24 points or higher but 26 points or lower

C: 21 points or higher but 23 points or lower

D: 18 points or higher but 20 points or lower

E: 17 points or lower

Evaluation Criteria: Examples B8 to B24 and Comparative Examples B3 to B6

A: 17 points or higher but 20 points or lower

B: 14 points or higher but 16 points or lower

C: 11 points or higher but 13 points or lower

D: 8 points or higher but 10 points or lower

E: 7 points or lower

TABLE B7-1

| | | Evaluation result | | | | | | | |
|---|---|---|---|---|---|---|---|---|---|
| | | Valuable producing efficiency | | | | | | | |
| | | Evaluation of valuable production | | | | Evaluation of matrix consumption | | | |
| | | Production rate A (%) | Production rate B (%) | C | Score | Matrix consumption ratio A (%) | Matrix consumption ratio B (%) | C | Score |
| Ex. B | 1 | 0.12 | 0.08 | 0.04 | 8 | 89 | 70 | 19 | 8 |
| | 2 | 0.18 | 0.13 | 0.05 | 10 | 93 | 69 | 24 | 10 |
| | 3 | 0.20 | 0.16 | 0.04 | 8 | 85 | 74 | 11 | 8 |
| | 4 | 0.20 | 0.16 | 0.04 | 8 | 91 | 67 | 24 | 10 |
| | 5 | 0.04 | 0.02 | 0.02 | 8 | 59 | 23 | 36 | 10 |
| | 6 | 0.01 | 0.00 | 0.01 | 8 | 20 | 2 | 18 | 8 |
| | 7 | 0.17 | 0.13 | 0.04 | 8 | 88 | 69 | 19 | 8 |
| Comp. | 1 | 0.01 | 0.05 | −0.04 | 0 | 13 | 70 | −57 | 0 |
| Ex. B | 2 | 0.03 | 0.03 | 0.00 | 0 | 80 | 72 | 8 | 5 |

TABLE B7-2

| | | Evaluation result | | | |
|---|---|---|---|---|---|
| | | Durability | | Total evaluation | |
| | | Number of times | Score | Score | Rating |
| Ex. B | 1 | 5 | 8 | 24 | C |
| | 2 | 4 | 6 | 26 | B |
| | 3 | 4 | 6 | 22 | C |
| | 4 | 4 | 6 | 24 | C |
| | 5 | 6 | 10 | 28 | A |
| | 6 | 6 | 10 | 26 | B |
| | 7 | 4 | 6 | 22 | C |
| Comp. | 1 | 4 | 6 | 6 | Failure |
| Ex. B | 2 | 2 | 2 | 7 | Failure |

FIG. 2A illustrates an electron microscopic image of the composite particles used in Example B2. FIG. 2B illustrates an electron microscopic image of the hydrophobic solid particles A used in Example B2. FIG. 2C illustrates an electron microscopic image of the hydrophobic solid particles B used in Example B2. FIG. 3A illustrates an image of the sample (biocatalyst-containing material) of Example B2. FIG. 3B illustrates an image of the sample (biocatalyst-containing material) of Comparative Example B6.

It was possible to observe a state that the surface of PTFE, which served as the hydrophobic solid particles A illustrated in FIG. 2B, was coated with hydrophobic silica, which served as the hydrophobic solid particles B illustrated in FIG. 2C, at a coating ratio of 100% as illustrated in FIG. 2A.

The sample (biocatalyst-containing material) obtained using the composite particles illustrated in FIG. 2A had a

TABLE B8

| | | Evaluation result | | | | | | | |
|---|---|---|---|---|---|---|---|---|---|
| | | Valuable producing efficiency | | | | | | | |
| | | Evaluation of matrix consumption | | | | Durability | | Total evaluation | |
| | | Matrix consumption ratio A (%) | Matrix consumption ratio B (%) | C | Score | Number of times | Score | Score | Rating |
| Ex. B | 8 | 88 | 71 | 19 | 8 | 4 | 6 | 14 | B |
| | 9 | 94 | 68 | 26 | 10 | 5 | 8 | 18 | A |
| | 10 | 91 | 69 | 22 | 10 | 6 | 10 | 20 | A |
| | 11 | 91 | 69 | 22 | 10 | 4 | 6 | 16 | B |
| | 12 | 91 | 69 | 22 | 10 | 5 | 8 | 18 | A |
| | 13 | 91 | 68 | 23 | 10 | 3 | 4 | 14 | B |
| | 14 | 92 | 67 | 25 | 10 | 4 | 6 | 16 | B |
| | 15 | 90 | 68 | 22 | 10 | 5 | 8 | 18 | A |
| | 16 | 91 | 67 | 24 | 10 | 3 | 4 | 14 | B |
| | 17 | 89 | 70 | 19 | 8 | 6 | 10 | 18 | A |
| | 18 | 90 | 68 | 22 | 10 | 5 | 8 | 18 | A |
| | 19 | 85 | 67 | 18 | 8 | 4 | 6 | 14 | B |
| | 20 | 92 | 69 | 23 | 10 | 3 | 4 | 14 | B |
| | 21 | 91 | 68 | 23 | 10 | 3 | 4 | 14 | B |
| | 22 | 91 | 70 | 21 | 10 | 2 | 2 | 12 | C |
| | 23 | 81 | 63 | 18 | 8 | 6 | 10 | 18 | A |
| | 24 | 90 | 67 | 23 | 10 | 2 | 2 | 12 | C |
| Comp. | 3 | 81 | 72 | 9 | 5 | 3 | 4 | 9 | D |
| Ex. B | 4 | — | 69 | — | — | — | — | — | Failure |
| | 5 | 91 | 71 | 20 | 10 | 1 | 0 | 10 | Failure |
| | 6 | 90 | 67 | 23 | 10 | 1 | 0 | 10 | Failure |

ratio (longer axis/shorter axis) of 1.34/1.31=1.02 between the length of the longer axis and the length of the shorter axis. As compared, a sample (biocatalyst-containing material) obtained using only hydrophobic silica serving as the hydrophobic solid particles B had a ratio (longer axis/shorter axis) of 1.43/1.31=1.09 between the length of the longer axis and the length of the shorter axis.

Aspects of the present disclosure are, for example, as follows.

<A1> Composite particles including:

a hydrophobic solid particle A; and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating Ratio } CR\ (\%) = \frac{\pi(d50b/2)^2}{4\pi(d50a/2+d50b/2)^2} \times \frac{\{X_b(\mathrm{g})/Y_b(\mathrm{g}/\mu\mathrm{m}^3)/Z_b(\mu\mathrm{m}^3)\}}{\{X_a(\mathrm{g})/Y_a(\mathrm{g}/\mu\mathrm{m}^3)/Z_a(\mu\mathrm{m}^3)\}} \times 100 \qquad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<A2> The composite particles according to <A1>, wherein at least one of the hydrophobic solid particle A and the hydrophobic solid particle B is at least one selected from the group consisting of fluororesins, silica, stearic acid-treated calcium carbonate, and hydrophobized starch.

<A3> The composite particles according to <A1> or <A2>, further including at least one selected from the group consisting of hydrophobic solid particles other than the hydrophobic solid particle A and the hydrophobic solid particle B that constitute the composite particles, and additives.

<A4> Composite particles including:

a hydrophobic solid particle A; and a hydrophobic solid particle B over a surface of the hydrophobic solid particle B, wherein a contact angle CALa of the hydrophobic solid particle A with a solution containing water in an amount of 15% by mass or greater is 100 degrees or greater but 180 degrees or less, wherein a contact angle CALb of the hydrophobic solid particle B with a solution containing water in an amount of 15% by mass or greater is 100 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2+d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \qquad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<A5> The composite particles according to <A4>, wherein the contact angle CALa of the hydrophobic solid particle A with the solution containing water in an amount of 15% by mass or greater is 100 degrees or greater but 160 degrees or less, and wherein the contact angle CALb of the hydrophobic solid particle B with the solution containing water in an amount of 15% by mass or greater is 100 degrees or greater but 160 degrees or less.

<A6> Liquid-encapsulating particles including:

a liquid droplet, and composite particles including a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, wherein a surface of the liquid droplet is coated with the composite particles, $$\text{Coating ratio } CR(\%) = \frac{\pi(d50b/2)^2}{4\pi(d50a/2+d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \qquad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<A7> Liquid-encapsulating particles including:

a liquid droplet formed of a solution containing water in an amount of 15% by mass or greater; and composite particles including a hydrophobic solid particle A and a hydrophobic solid particle B over a surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, wherein a surface of the liquid droplet is coated with the composite particles, Formula 1

$$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<A8> The liquid-encapsulating particles according to <A7>, wherein the contact angle CALa of the hydrophobic solid particle A with the solution containing water in an amount of 15% by mass or greater is 100 degrees or greater but 160 degrees or less, and wherein the contact angle CALb of the hydrophobic solid particle B with the solution containing water in an amount of 15% by mass or greater is 100 degrees or greater but 160 degrees or less.

<A9> The liquid-encapsulating particles according to any one of <A6> to <A8>, wherein a number average particle diameter d50c of the liquid-encapsulating particles is 15 micrometers or greater but 2.5 mm or less.

<A10> The liquid-encapsulating particles according to any one of <A6> to <A9>, wherein the liquid droplet contains at least one selected from the group consisting of food additives and physiologically active substances.

<A11> Composite particles for forming liquid-encapsulating particles, the composite particles including:

the composite particles according to any one of <A1> to <A5>.

<A12> A method for producing liquid-encapsulating particles, the method including:

forming a liquid droplet from a liquid; and coating a surface of the liquid droplet with composite particles including a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, Formula 1

$$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<A13> The method for producing the liquid-encapsulating particles according to <A12>, the method further including separating the composite particles left unused for coating the surface in the coating, from the liquid-encapsulating particles.

<A14> An apparatus for producing liquid-encapsulating particles, the apparatus including:

a liquid droplet forming unit configured to form a liquid droplet from a liquid; and a surface coating unit configured to coat a surface of the liquid droplet with composite particles including a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<A15> The apparatus for producing the liquid-encapsulating particles according to <A14>, the apparatus further including a separating unit configured to separate the composite particles left unused for coating the surface by the surface coating unit, from the liquid-encapsulating particles.

<B1> A biocatalyst-containing material including:

a liquid droplet containing a biocatalyst; and composite particles coating a surface of the liquid droplet, wherein a number average particle diameter d50c of the biocatalyst-containing material is 10 micrometers or greater but 1,000 micrometers or less.

<B2> The biocatalyst-containing material according to <B1>, wherein the composite particles include a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<B3> The biocatalyst-containing material according to <B1>, wherein the liquid droplet is formed of a solution containing water in an amount of 15% by mass or greater, wherein the composite particles include a hydrophobic solid particle A and a hydrophobic solid particle B over the surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<B4> The biocatalyst-containing material according to <B2> or <B3>, wherein at least one of the hydrophobic solid particle A and the hydrophobic solid particle B is at least one selected from the group consisting of fluororesins, silica, stearic acid-treated calcium carbonate, and hydrophobized starch.

<B5> The biocatalyst-containing material according to any-one of <B1> to <B4>, wherein the biocatalyst is at least one selected from the group consisting of animal cells, plant cells, microorganisms, and enzymes.

<B6> The biocatalyst-containing material according to any-one of <B1> to <B4>, wherein the number average particle diameter d50c is 500 micrometers or greater but 800 micrometers or less.

<B7> The biocatalyst-containing material according to any-one of <B1> to <B6>, wherein the liquid droplet contains at least one selected from the group consisting of food additives and physiologically active substances.

<B8> A biocatalyst-containing material producing apparatus including:

a liquid droplet forming unit configured to form a liquid droplet from a liquid containing a biocatalyst; and a surface coating unit configured to coat a surface of the liquid droplet with composite particles including a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2+d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<B9> A biocatalyst-containing material producing method including:

forming a liquid droplet from a liquid containing a biocatalyst; and coating a surface of the liquid droplet with composite particles including a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2+d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<B10> A biocatalyst-containing material producing apparatus including:

a liquid droplet forming unit configured to form a liquid droplet from a solution containing a biocatalyst and water in an amount of 15% by mass or greater; and a surface coating unit configured to coat a surface of the liquid droplet with composite particles including a hydrophobic solid particle A and a hydrophobic solid particle B over a surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2+d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

<B11> A biocatalyst-containing material producing method including:

forming a liquid droplet from a solution containing a biocatalyst and water in an amount of 15% by mass or greater; and coating a surface of the liquid droplet with composite particles including a hydrophobic solid particle A and a hydrophobic solid particle B over a surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2+d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

The composite particles according to any one of <A1> to <A5>, the liquid-encapsulating particles according to any one of <A6> to <A10>, the composite particles for forming liquid-encapsulating particles according to <A11>, the method for producing liquid-encapsulating particles according to <A12> or <A13>, the apparatus for producing liquid-encapsulating particles according to <A14> or <A15>, the biocatalyst-containing material according to any one of <B1> to <B7>, the biocatalyst-containing material producing apparatus according to <B8> or <B10>, and the biocatalyst-containing material producing method according to <B9> or <B11> can solve the various problems in the related art and achieve the object of the present disclosure.

What is claimed is:

1. Composite particles comprising:

a hydrophobic solid particle A; and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density(g/cubic micrometer) of the hydrophobic solid particle A, Yb represents a dens (g/cubic micrometer) of the hydrophobic solid particle B, Za represents a volume (cubic micrometer) of the hydrophobic solid particle A, and Zb represents a volume (cubic micrometer) of the hydrophobic solid particle B.

2. The composite particles according to claim 1, wherein at least one of the hydrophobic solid particle A and the hydrophobic solid particle B comprises at least one selected from the group consisting of fluororesins, silica, stearic acid-treated calcium carbonate, and hydrophobized starch.

3. The composite particles according to claim 1, further comprising at least one selected from the group consisting of hydrophobic solid particles other than the hydrophobic solid particle A and the hydrophobic solid particle B that constitute the composite particles, and additives.

4. Composite particles for forming liquid-encapsulating particles, the composite particles comprising:

the composite particles according to claim 1.

5. A biocatalyst-containing material producing method comprising:

forming a liquid droplet from a liquid containing a biocatalyst; and coating a surface of the liquid droplet with the composite particles according to claim 1.

6. A method for producing liquid-encapsulating particles, the method comprising:

forming a liquid droplet from a liquid; and coating a surface of the liquid droplet with the composite particles according to claim 1.

7. The method for producing the liquid-encapsulating, particles according to claim 6, the method further comprising separating the composite particles left unused for coating the surface in the coating, from the liquid-encapsulating particles.

8. A biocatalyst-containing material comprising:

a liquid droplet containing a biocatalyst; and the composite particles according to claim 1, coating a surface of the liquid droplet, wherein a number average particle diameter d50c of the biocatalyst-containing material is 10 micrometers or greater but 1,000 micrometers or less.

9. The biocatalyst-containing material according to claim 8, wherein the composite particles include a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, $$\text{Coating ratio } CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100 \quad \text{Formula 1}$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

10. The biocatalyst-containing material according to claim 9, wherein at least one of the hydrophobic solid particle A and the hydrophobic solid particle B comprises at least one selected from the group consisting of fluororesins, silica, stearic acid-treated calcium carbonate, and hydrophobized starch.

11. The biocatalyst-containing material according to claim 8, wherein the liquid droplet is formed of a solution containing water in an amount of 15% by mass or greater, wherein the composite particles include a hydrophobic solid particle A and a hydrophobic solid particle B over a surface of the hydrophobic solid particle A, wherein a contact angle CALa of the hydrophobic solid particle A with the solution is 100 degrees or greater but 180 degrees or less, wherein a contact angle CALb of the hydrophobic solid particle B with the solution is 100 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, Formula 1

$$\text{Coating ratio}\,CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

12. The biocatalyst-containing material according to claim 8, wherein the biocatalyst comprises at least one selected from the group consisting of animal cells, plant cells, microorganisms, and enzymes.

13. The biocatalyst-containing material according to claim 8, wherein the number average particle diameter d50c is 500 micrometers or greater but 800 micrometers or less.

14. The biocatalyst-containing material according to claim 8, wherein the liquid droplet contains at least one selected from the group consisting of food additives and physiologically active substances.

15. Liquid-encapsulating particles comprising:

a liquid droplet; and composite particles including a hydrophobic solid particle A and a hydrophobic solid particle B over a surface of the hydrophobic solid particle A, wherein a contact angle CAa of the hydrophobic solid particle A with water is 110 degrees or greater but 180 degrees or less, wherein a contact angle CAb of the hydrophobic solid particle B with water is 110 degrees or greater but 180 degrees or less, wherein a ratio (d50a/d50b) of a number average particle diameter d50a of the hydrophobic solid particle A to a number average particle diameter d50b of the hydrophobic solid particle B is 10 or greater but 100 or less, and wherein a coating ratio CR of the composite particles expressed by Formula 1 below is 50% or higher but 500% or lower, wherein a surface of the liquid droplet is coated with the composite particles, Formula 1

$$\text{Coating ratio}\,CR(\%) = \frac{\pi(d50b/2)^2}{4\pi(d50a/2 + d50b/2)^2} \times \frac{[X_b(g)/Y_b(g/\mu m^3)/Z_b(\mu m^3)]}{[X_a(g)/Y_a(g/\mu m^3)/Z_a(\mu m^3)]} \times 100$$

where in Formula 1, Xa represents a mass (g) of the hydrophobic solid particle A, Xb represents a mass (g) of the hydrophobic solid particle B, Ya represents a density (g/cubic micrometer) of the hydrophobic solid particle A, Yb represents a density (g/cubic micrometer) of the hydrophobic solid particle B, Za represents a volume (cubic micrometer) of the hydrophobic solid particle A, and Zb represents a volume (cubic micrometer) of the hydrophobic solid particle B.

16. The liquid-encapsulating particles according to claim 15, wherein the liquid droplet comprises a solution containing water in an amount of 15% by mass or greater, and less than 100%, the solution further comprising a solute, wherein a contact angle CALa of the hydrophobic solid particle A with the solution is 100 degrees or greater but 180 degrees or less, and wherein a contact angle CALb of the hydrophobic solid particle B with the solution is 100 degrees or greater but 180 degrees or less.

17. The liquid-encapsulating particles according to claim 15, wherein a number average particle diameter d50c of the liquid-encapsulating particles is 15 micrometers or greater but 2.5 mm or less.

18. The liquid-encapsulating particles according to claim 15, wherein the liquid droplet contains at least one selected from the group consisting of food additives and physiologically active substances.

* * * * *